(12) United States Patent
Levinson et al.

(10) Patent No.: US 6,190,909 B1
(45) Date of Patent: Feb. 20, 2001

(54) TH2-SPECIFIC GENE

(75) Inventors: Doug Levinson, Sherborn; Wei Gu, Brookline; Sophie Lehar, Boston, all of MA (US)

(73) Assignee: Millennium Pharmaceuticals, Inc., Cambridge, MA (US)

(*) Notice: Under 35 U.S.C. 154(b), the term of this patent shall be extended for 0 days.

(21) Appl. No.: 08/884,077

(22) Filed: Jun. 25, 1997

Related U.S. Application Data

(63) Continuation-in-part of application No. 08/841,901, filed on Apr. 17, 1997.
(51) Int. Cl.$^7$ .......................... C07H 21/04; C12N 15/12; C12N 15/85
(52) U.S. Cl. ...................... 435/325; 435/69.1; 435/320.1; 435/354; 435/355; 536/23.1; 536/23.5
(58) Field of Search .................................. 435/69.1, 325, 435/354, 320.1, 343.1, 463, 355; 530/350; 536/23.1, 23.5, 24.31, 24.33

(56) References Cited

U.S. PATENT DOCUMENTS 5,116,964 * 5/1992 Capon et al. ...................... 536/23.5

FOREIGN PATENT DOCUMENTS

WO 95/11986 * 5/1995 (WO).
WO98/28425 * 7/1998 (WO).

OTHER PUBLICATIONS

E.–L. Winnacker, "From Genes to Clones", VCH Publishers, New York, NY, (1987). pp. 198–204, 239, 246–253, 263–266, 328–343.*

Seder, R.A. et al., 1995, "The Functional Role of CD8+ T Helper Type 2 Cells", J. Exp. Med. 181:5–7.*

Gavett, S.H. et al., 1994, "Depletion of Murine CD4+ T Lymphocytes Prevents Antigen–induced Airway Hyperactivity and Pulmonary Eosinophilia", Am. J. Respir. Cell Mol. Biol. 10:587–593.*

Kaneshima, H. et al., 1994, "Human hematolymphoid cells in SCID mice", Curr. Opin. Imm. 6:327–333.*

Luckas, N.W. et al., 1994, "Interleukin–4–dependent Pulmonary Eosinophil Infiltration in a Murien Model of Asthma", Am. J. Respir. Cell Mol. Biol. 10:526–532.*

Maggi, E. et al., 1994, "the Th2–like CD8+ T Cells Showing B Cell Helper Function and Reduced Cytolytic Activity in Human Immunodeficiency Virus Type 1 Infection", J. Exp. Med. 180:489–495.*

Maggi, E. et al., 1994, "Ability of HIV to promote a $T_H1$ to $T_H0$ Shift and to Replicate Preferentially in $T_H2$ and $T_H0$ Cells", Science 265:244.*

Manetti, R. et al., 1994, "CD30 Expression by CD8+ T Cells Producing Type 2 Helper Cytokines. Evidence for Large Numbers of CD8+ CD30+ T Cell Clones in Human Immunodeficiency Virus Infection", J. Exp. Med. 180:2407–2411.*

Platt, K.A., 1994, "Independent Regulation of Adipose Tissue–specificity and Obesity Response of the Adipsin Promoter in Transgenic Mice", J. Biol. Chem. 269:28558–28562.*

Chen, J. et al., 1993, "RAG–2–deficient blastocyst complementation: An assay of gene function in lymphocyte development", PNAS USA 90:4528–4532.*

Clerci, M. et al., 1993, "Changes in Interleukin–4 Production in Asymptomatic, Human Immunodeficiency Virus–seropositive Individulas", J. Clin. Invest. 91:759.*

Clerci, M. et al., 1993, "Restoration of HIV–Specific Cell–Mediated Immune Responses by Interleukin–12 in Vitro", Science 262:1721.*

Kanagawa, B. et al., 1993, "Resistance of Mice Deficient in IL–4 to Retrovirus–Induced Immunodeficiency Syndrome (MAIDS)", Science 262:240.*

(List continued on next page.)

Primary Examiner—John L. LeGuyader
Assistant Examiner—Mark L. Shibuya
(74) Attorney, Agent, or Firm—Pennie & Edmonds LLP

(57) ABSTRACT

The present invention relates to the discovery, identification and characterization of nucleic acids that encode a novel protein differentially expressed within the TH2 cell subpopulation (hereinafter referred to as STIF). The invention encompasses STIF nucleotides, host cell expression systems, STIF proteins, fusion proteins, polypeptides and peptides, antibodies to the STIF protein, transgenic animals that express a STIF transgene, or recombinant knock-out animals that do not express the STIF protein, and compounds that modulate STIF gene expression or STIF activity that can be used for diagnosis, drug screening, clinical trial monitoring, and/or used to treat STIF based disorders, such as proliferative disorders and T-lymphocyte-related disorders including, but not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

17 Claims, 6 Drawing Sheets

OTHER PUBLICATIONS

Robinson, D. et al., 1993, "Activation of CD4+ T cells, increased $T_{H2}$–type cytokine mRNA expression, and eosinophil recruitment in bronchoalveolar lavage after allergen inhalation challenge in patients with atopic asthma", J. Allergy Clin. Imm. 92:313.*

McConnell, H.M. et al., 1992, "The Cytosensor Microphysiometer: Biological Applications of Silicon Technology", Science 257:1906.*

Shinkai, Y. et al., 1992, "RAG–2–Deficient Mice Lack Mature Lymphocytes Owing to Inability to Initiate V(D)J Rearrangement", Cell 68:855–867.* de Waal Malefyt et al., 1991, "Interleukin 10 (IL–10) Inhibits Cytokine Synthesis by Human Monocytes: An Autoregulatory Role of IL–10 Produced by Monocytes", J. Exp. Med. 174:1209–1220.*

Del Prete, A.F. et al., 1991, "Purified Protein Derivative of Mycobacterium tuberculosis and Excretory–Secretory Antigen(s) of *Toxocara canis* Expand In Vitro Human T Cells with Stable and Opposite (Type 1 T Helper or Type 2 T Helper) Profile of Cytokine Production", J. Clin. Invest. 88:346.*

Mosman, T.R. & Moore, 1991, "The role of IL–10 in crossregulation of $T_H1$ and $T_H2$ responses", Immunol. Today 12:49.*

Yamamura, M. et al., 1991, "Defining Protective Responses to Pathogens: Cytokine Profiles in Leprosy Lesions", Science 254:277.*

Makino, M. et al., 1990, "H–2–Associated and Background Genes Influence the Development of a Murine Retrovirus–Induced Immunodeficiency Syndrome", J. Imm. 144:4347.*

Weirnenga, E.A. et al., 1990, "Evidence for Compartmentalization of Functional Subsets of CD4+ T Lymphocytes in Atopic Patients", J. Imm. 144:4651.*

Askew, et al., 1989, "Molecular Recognition with Convergent Functional Groups. Synthetic and Structural Studies with a Model Receptor for Nucleic Acid Components", J. Am. Chem. Soc. 111:1082–1090.*

Firestein, G.S. et al., 1989, "A New Murine CD4+ T Cell Subset with an Unresticted Cytokine Profile", J. Imm. 143:518.*

Mosman, T.R. & Coffman, R.L., 1989, "TH1 and TH2 Cells: Different Patterns of Lymphokine Secretion Lead to Different Functional Properties", Ann. Rev. Immunol. 7:145.*

Miyajima et al., 1986, "Expression of murine and human granulocyte–macrophage colony–stimulating factors in S. cerevisiae: mutagenesis of the potential", EMBO J. 5(6):1193–1197.*

* cited by examiner

```
1   CGA CCC ACG CGT CCG ATC ATT TCC ACA GCT GAG AAG GAG CTT CCC

46  ACC CAG CAG AAG ATC CTC TAC CAA TGA ATG CTG ACT GAG CCT GCC
                                        MET Leu Thr Glu Pro Ala   6

91  CAC CTT TTT GTG CAC AAG AAG AAC CAG CCA CCT TCA CAC AGC AGC
    Gln Leu Phe Val His Lys Lys Asn Gln Pro Pro Ser His Ser Ser  21

136 CTC CGG CTT CAC TTT AGG ACC CTA GCA GGA GCA CTG GCC CTT TCT
    Leu Arg Leu His Phe Arg Thr Leu Ala Gly Ala Leu Ala Leu Ser  36

181 TCA ACA CAG ATG AGT TGG GGA CTA CAG ATT CTC CCC TGC CTG AGC
    Ser Thr Gln MET Ser Trp Gly Leu Gln Ile Leu Pro Cys Leu Ser  51

226 CTA ATC CTT CTT CTT TGG AAC CAA GTG CCA GGG CTT GAG GGT CAA
    Leu Ile Leu Leu Leu Trp Asn Gln Val Pro Gly Leu Glu Gly Gln  66

271 GAG TTC CGA TTT GGG TCT TGC CAA GTG ACA GGG GTG GTT CTC CCA
    Glu Phe Arg Phe Gly Ser Cys Gln Val Thr Gly Val Val Leu Pro  81

316 GAA CTG TGG GAG GCC TCC TGG ACT GTG AAG AAC ACT GTG CAA ACT
    Glu Leu Trp Glu Ala Ser Trp Thr Val Lys Asn Thr Val Gln Thr  96

361 CAG GAT GAC ATC ACA AGC ATC CGG CTG TTG AAG CCG CAG GTT CTG
    Gln Asp Asp Ile Thr Ser Ile Arg Leu Leu Lys Pro Gln Val Leu 111

406 CGG AAT GTC TCG GGT GCT GAG AGC TGT TAC CTT GCC CAC AGC CTG
    Arg Asn Val Ser Gly Ala Glu Ser Cys Tyr Leu Ala His Ser Leu 126

451 CTG AAG TTC TAC TTG AAC ACT GTT TTC AAG AAC TAC CAC AGC AAA
    Leu Lys Phe Tyr Leu Asn Thr Val Phe Lys Asn Tyr His Ser Lys 141

496 ATA GCC AAA TTC AAG GTC TTG AGG TCA TTC TCC ACT CTG GCC AAC
    Ile Ala Lys Phe Lys Val Leu Arg Ser Phe Ser Thr Leu Ala Asn 156

541 AAC TTC ATA GTC ATC ATG TCA CAA CTA CAG CCC AGT AAG GAC AAT
    Asn Phe Ile Val Ile MET Ser Gln Leu Gln Pro Ser Lys Asp Asn 171

586 TCC ATG CTT CCC ATT AGT GAG AGT GCA CAC CAG CGG TTT TTG CTG
    Ser MET Leu Pro Ile Ser Glu Ser Ala His Gln Arg Phe Leu Leu 186

631 TTC CGC AGA GCA TTC AAA CAG TTG GAT ACA GAA GTC GCT TTG GTG
    Phe Arg Arg Ala Phe Lys Gln Leu Asp Thr Glu Val Ala Leu Val 201

676 AAA GCC TTT GGG GAA GTG GAC ATT CTC CTG ACC TGG ATG CAG AAA
    Lys Ala Phe Gly Glu Val Asp Ile Leu Leu Thr Trp MET Gln Lys 216

721 TTC TAC CAT CTC TGA CTG CTG ATT GGA TAA CTT CCT CCT TTG CTC
    Phe Tyr His Leu STP
```

FIG.1A

766 TCC ATG CCA TTT CAA GGC ATT GTG TAC ATC CCT GCT GTC CTC AAG

811 GCA CTT CAG ACC CTT GGC CAT GGA CCC CGT TGT TGG CTC AGG CTT

856 TTC CTC AGA CCT CAC TCT TCA GTC CAA ATG ACA GCC ATA GAT GGC

901 ACC TTT GGA TGC TCC GAC TGA CCC ACA AAG TAG ATT TGC ATA TTT

946 ATT ACA GCC CTA TTA AAT TAT TGT CAC CTT CCC TGG AAA CCG TAT

991 TTA TTT GTG AGA CCA GAA GTT CCA TGA A

FIG.1B

GTCGACCCACGGCTCCGCTGAAATGACTTCCACGGCTGGGACGGGAACCTTCCACCCACAGCTATGCCTCTGATTGGTG
AATGGTGAAGGTGCCTGTCTAACTTTTCTGTAAAAAGAACCAGTGCCTCCAGGCAGCCAGCCCTCAAGCATCACTTAC

```
                                            M   Q   M   V   L   P
AGGACCAGAGCAGACCCTTCTGCCCTCCCTTTGCTGGCGACAGCCTCTCAA ATG CAG ATG GTT CTC CCT

C   L   G   F   T   L   L   L   W   S   Q   V   S   G   A   Q   G   Q   E   F
TGC CTG GGT TTT ACC CTG CTT CTC TGG AGC CAG GTA TCA GGG GCC CAG GGC CAA GAA TTC

H   F   G   P   C   Q   V   K   G   V   V   P   Q   K   L   W   E   A   F   W
CAC TTT GGG CCC TGC CAA GTG AAG GGG GTT GTT CCC CAG AAA CTG TGG GAA GCC TTC TGG

A   V   K   D   T   M   Q   A   Q   D   N   I   T   S   A   R   L   L   Q   Q
GCT GTG AAA GAC ACT ATG CAA GCT CAG GAT AAC ATC ACG AGT GCC CGG CTG CTG CAG CAG

E   V   L   Q   N   V   S   D   A   E   S   C   Y   L   V   H   T   L   L   E
GAG GTT CTG CAG AAC GTC TCG GAT GCT GAG AGC TGT TAC CTT GTC CAC ACC CTG CTG GAG

F   Y   L   K   T   V   F   K   N   Y   H   N   R   T   V   E   V   R   T   L
TTC TAC TTG AAA ACT GTT TTC AAA AAC TAC CAC AAT AGA ACA GTT GAA GTC AGG ACT CTG

K   S   F   S   T   L   A   N   N   F   V   L   I   V   S   Q   L   Q   P   S
AAG TCA TTC TCT ACT CTG GCC AAC AAC TTT GTT CTC ATC GTG TCA CAA CTG CAA CCC AGT

Q   E   N   E   M   F   S   I   R   D   S   A   H   R   R   F   L   L   F   R
CAA GAA AAT GAG ATG TTT TCC ATC AGA GAC AGT GCA CAC AGG CGG TTT CTG CTA TTC CGG

R   A   F   K   Q   L   D   V   E   A   A   L   T   K   A   L   G   E   V   D
AGA GCA TTC AAA CAG TTG GAC GTA GAA GCA GCT CTG ACC AAA GCC CTT GGG GAA GTG GAC

I   L   L   T   W   M   Q   K   F   Y   K   L   *
ATT CTT CTG ACC TGG ATG CAG AAA TTC TAC AAG CTC TGA
```

FIG.2A

ATGTCTAGACCAGGACCTCCCTCCCCCTGGCACTGGTTTGTTCCCTGTGTCATTTCAAACAGTCTCCCTTCCTATGCTG

TTCACTGGACACTTCAGCGCCCTTGGCCATGGGTCCCCATTCTTGGCCCAGGATTATTGTCAAAGAAGTCATTCTTTAAGC

AGCGCCCAGTGACAGTCAGGGAAGGTGCCTCTGGATGCTGTGAAGAGTCTACAGAGAAGATTCTGTATTTATTACAACT

CTATTAATTAATGTCAGTATTTCAACTGAAGTTCTATTTATTTGTGAGACTGTAAGTTACATGAAGGCAGCAGAATAT

FIG.2B

TGTGCCCCATGCTTCTTTACCCCTCACAATCCTTGCCACAGTGTGGGGCAGTGGATGGGTGCTTAGTAAGTACTTAATA

AACTGTGGTGCTTTTTTGGCCTGTCTTTGGATTGTTAAAAAACAGAGAGGGATGCTTGGATGTAAAACTGAACTTCAG

AGCATGAAAATCACACTGTCTTCTGATATCTGCAGGGACAGAGCATTGGGGTGGGGTAAGGTGCATCTGTTTGAAAAG

TAAACGATAAAAATGTGGATTAAAGTGCCCAGCACACAAAGCAGATCCTCAATAAACATTTCATTTCCCACCCACACTCGCC

AGCTCACCCCATCATCCCTTGGTGCCCTCCTTTTTTTTATCCTAGTCATTCTTCCCTAATCTTCCACTTGA

GTGTCAAGCTGACCTTGCTGACATTGCACCTGGATGTACTATCCAATCTGTGATGACATTCCCTGCTAATAAA

AGACAACATAACTCAAAAAAAAAAAAAAA

FIG.2C

| | | | | | | | | | | |
|---|---|---|---|---|---|---|---|---|---|---|
| M | N | F | Q | R | L | Q | S | L | W | T | L | A | S | R | P | F | C | P | 20 |
| ATG | AAT | TTT | CAA | CAG | AGG | CTG | CAA | AGC | CTG | TGG | ACT | TTA | GCC | AGC | AGA | CCC | TTC | TGC | CCT | 60 |

| P | L | A | T | A | S | Q | M | Q | M | V | L | P | C | L | G | F | T | 40 |
| CCT | TTG | CTG | ACA | GCC | TCT | CAA | ATG | CAG | ATG | GTT | CTC | CCT | TGC | CTG | GGT | TTT | ACC | 120 |

| L | L | W | S | Q | V | S | G | A | Q | G | K | L | W | E | A | F | H | F | G | P | C | 60 |
| CTG | CTT | CTC | TGG | AGC | CAG | GTA | TCA | GGG | GCC | CAG | GGC | AAA | CTG | TGG | GAA | GCC | TTC | CAC | TTT | GGG | CCC | TGC | 180 |

| Q | V | K | G | V | P | V | Q | K | L | Q | R | L | E | A | Q | V | K | D | T | 80 |
| CAA | GTG | AAG | GGG | GTT | CCC | GTT | CAG | AAA | CTG | CAG | CGG | CTG | GAA | GCT | CAG | GTT | AAA | GAC | ACT | 240 |

| M | Q | A | Q | D | N | I | T | S | A | R | L | H | T | L | E | V | L | Q | N | 100 |
| ATG | CAA | GCT | CAG | GAT | AAC | ATC | ACG | AGT | GCC | CGG | CTG | CAC | ACC | CTG | GAG | GTT | CTG | CAG | AAC | 300 |

| V | S | D | A | E | S | C | Y | L | V | E | R | T | V | Q | L | F | Y | L | K | S | T | 120 |
| GTC | TCG | GAT | GCT | GAG | AGC | TGT | TAC | CTT | GTC | GAG | AGG | ACA | GTT | CAA | CTG | TTC | TAC | TTG | AAG | TCA | ACT | 360 |

| V | F | K | N | Y | H | N | R | T | A | H | R | T | L | K | S | Q | E | N | E | M | T | 140 |
| GTT | TTC | AAA | AAC | TAC | CAC | AAT | AGA | ACA | GCA | CAC | AGG | ACT | CTG | AAG | TCA | CAA | GAA | AAT | GAG | ATG | ACT | 420 |

| L | A | N | N | F | V | L | I | V | S | A | H | R | R | F | L | L | P | F | R | A | F | K | Q | 160 |
| CTG | GCC | AAC | AAC | TTT | GTT | CTC | ATC | GTG | AGT | GCA | CAC | AGG | CGG | TTT | CTG | CTA | CCC | TTC | CGG | AGA | TTC | AAA | CAG | 480 |

| F | S | I | R | D | S | A | A | L | T | K | A | L | G | E | V | D | I | L | L | T | W | M | 180 |
| TTT | TCC | ATC | AGA | GAC | AGT | GCA | GCT | CTG | ACC | AAA | GCC | CTT | GGG | GAA | GTG | GAC | ATT | CTT | CTG | ACC | TGG | ATG | 540 |

| L | D | V | E | A | A | T | K | Q | A | F | N | K | Q | 200 |
| TTG | GAC | GTA | GAA | GCA | GCA | ACC | AAA | CAG | GCC | TTC | AAT | AAA | CAG | 600 |

| M | Q | K | F | Y | K | L | * | 208 |
| CAG | AAA | TTC | TAC | AAG | CTC | TGA | | 624 |

FIG. 3

TH2-SPECIFIC GENE

This is a Continuation-In-Part of Ser. No. 08/841,901, filed Apr. 17, 1997, which is incorporated herein by reference in its entirety.

1. INTRODUCTION

The present invention relates to the discovery, identification and characterization of nucleic acids that encode a novel protein differentially expressed within the TH2 cell subpopulation (hereinafter referred to as STIF). The invention encompasses STIF nucleotides, host cell expression systems, STIF proteins, fusion proteins, polypeptides and peptides, antibodies to the STIF protein, transgenic animals that express a STIF transgene, or recombinant knock-out animals that do not express the STIF protein, and compounds that modulate STIF gene expression or STIF activity that can be used for diagnosis, drug screening, clinical trial monitoring, and/or used to treat STIF based disorders, such as proliferative disorders and T-lymphocyte-related disorders including, but not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

2. BACKGROUND OF THE INVENTION

Two distinct types of T lymphocytes are recognized: $CD8^+$ cytotoxic T lymphocytes (CTLs) and $CD4^+$ helper T lymphocytes (TH cells). CTLs recognize and kill cells which display foreign antigens on their surfaces. CTL precursors display T cell receptors that recognize processed peptides derived from foreign proteins, in conjunction with class I MHC molecules, on other cell surfaces. This recognition process triggers the activation, maturation and proliferation of the precursor CTLS, resulting in CTL clones capable of destroying the cells exhibiting the antigens recognized as foreign.

TH cells are involved in both humoral and cell-mediated forms of effector immune responses. With respect to the humoral, or antibody, immune response, antibodies are produced by B lymphocytes through interactions with TH cells. Specifically, extracellular antigens are endocytosed by antigen-presenting cells (APCs), processed, and presented preferentially in association with class II major histocompatibility complex (MHC) molecules to $CD4^+$ class II MHC-restricted TH cells. These TH cells in turn activate B lymphocytes, resulting in antibody production.

The cell-mediated, or cellular, immune response, functions to neutralize microbes which inhabit intracellular locations. Foreign antigens, such as, for example, viral antigens, are synthesized within infected cells and presented on the surfaces of such cells in association with class I MHC molecules. This, then, leads to the stimulation of the $CD8^+$ class I MHC-restricted CTLs.

Some agents, such as mycobacteria, which cause tuberculosis and leprosy, are engulfed by macrophages and processed in vacuoles containing proteolytic enzymes and other toxic substances. While these macrophage components are capable of killing and digesting most microbes, agents such as mycobacteria survive and multiply. The agents' antigens are processed, though, by the macrophages and presented preferentially in association with class II MHC molecules to $CD4^+$ class II MHC-restricted TH cells, which become stimulated to secrete interferon-, which, in turn, activates macrophages. Such activation results in the cells' exhibiting increased bacteriocidal ability.

TH cells are composed of at least two distinct subpopulations, termed TH1 and TH2 cell subpopulations. Evidence suggests that TH1 and TH2 subtypes represent extremely polarized populations of TH cells. While such subpopulations were originally discovered in murine systems (reviewed in Mosmann, T. R. and Coffman, R. L., 1989, Ann. Rev. Immunol. 7:145), the existence of TH1- and TH2-like subpopulations has also been established in humans (Del Prete, A. F. et al., 1991, J. Clin. Invest. 88:346; Wiernenga, E. A. et al., 1990, J. Imm. 144:4651; Yamamura, M. et al., 1991, Science 254:277; Robinson, D. et al., 1993, J. Allergy Clin. Imm. 92:313). While TH1-like and TH2-like cells can represent the most extremely polarized TH cell subpopulations, other TH cell subpopulations, such as THO cells (Firestein, G. S. et al., 1989, J. Imm. 143:518), which represent TH cells which have characteristics of TH1 and TH2 cell subpopulations.

TH1-like and TH2-like cells appear to function as part of the different effector functions of the immune system (Mosmann, T. R. and Coffmann, R. L., 1989, Ann. Rev. Imm. 7:145). Specifically, TH1-like cells direct the development of cell-mediated immunity, triggering phagocyte-mediated host defenses, and are associated with delayed hypersensitivity. Accordingly, infections with intracellular microbes tend to induce TH1-type responses. TH2 cells drive humoral immune responses, which are associated with, for example, defenses against certain helminthic parasites, and are involved in antibody and allergic responses.

It has been noted that the ability of the different TH cell types to drive different immune effector responses is due to the exclusive combinations of cytokines which are expressed within a particular TH cell subpopulation. For example, TH1 cells are known to secrete interleukin-2 (IL-2), interferon-$\gamma$ (IFN-$\gamma$), and lymphotoxin, while TH2 cells secrete interleukin-4 (IL-4), interleukin-5 (IL-5), and interleukin-10 (IL-10).

It is thought that TH1 and TH2 subpopulations arise from a common naive precursor (referred to as THP). For example, naive $CD4^+$ cells from mice which express a single transgenic T cell receptor can be induced to develop into either the TH1 or TH2 cell type. The conditions of antigen stimulation, including the nature and amount of antigen involved, the type of antigen-presenting cells, and the type of hormone and cytokine molecules present seem to all represent determinants of the pattern of TH1 versus TH2 differentiation, with, perhaps, the decisive role belonging to the cytokines present. With such a complex series of possible determinants, a full accounting of the exact factors important in driving TH1 or TH2 differentiation are, as yet largely unknown.

Further, it has recently been noted that, in addition to $CD4^+$ TH cells, $CD8^+$ CTLs can, under certain conditions, also exhibit TH1-like or TH2-like cytokine profiles (Seder, R. A. et al., 1995, J. Exp. Med. 181:5–7; Manetti, R. et al., 1994, J. Exp. Med. 180:2407–2411; Maggi, E. et al., 1994, J. Exp. Med. 180:489–495). While the precise functional role of such $CD8^+$ TH-like cells is currently unknown, these cell subpopulations appear to have great relevance to immune responses against infectious agents such as viruses and intracellular parasites.

Once TH1 and TH2 subpopulations are expanded, the cell types tend to negatively regulate one another through the actions of cytokines unique to each. For example, TH1-produced IFN-γ negatively regulates TH2 cells, while TH2-produced IL-10 negatively regulates TH1 cells. Moreover, cytokines produced by TH1 and TH2 antagonize the effector functions of one another (Mosmann, T. R. and Moore, 1991, Immunol. Today 12:49).

Failure to control or resolve an infectious process often results from an inappropriate, rather than an insufficient immune response, and can underlie a variety of distinct immunological disorders. Such disorders can include, for example, atopic conditions (i.e., IgE-mediated allergic conditions) such as asthma, allergy, including allergic rhinitis, dermatitis, including psoriasis, pathogen susceptibilities, chronic inflammatory disease, organ-specific autoimmunity, graft rejection and graft versus host disease. For example, nonhealing forms of human and murine leishmaniasis result from strong but counterproductive TH2-like-dominated immune responses. Lepromatous leprosy also appears to feature a prevalent, but inappropriate, TH2-like response.

It is possible that another example can be HIV infection. Here, it has been suggested that a drop in the ratio of TH1-like cells to other TH cell subpopulations can play a critical role in the progression toward disease symptoms. Further, it has been noted that, at least in vitro, TH2-like clones appear to be more efficient supporters of HIV viral replication than TH1-like clones.

Further, while TH1-mediated inflammatory responses to many pathogenic microorganisms are beneficial, such responses to self antigens are usually deleterious. It has been suggested that the preferential activation of TH1-like responses is central to the pathogenesis of such human inflammatory autoimmune diseases as multiple sclerosis and insulin-dependent diabetes. For example, TH1-type cytokines predominate in the cerebrospinal fluid of patients with multiple sclerosis, pancreases of insulin-dependent diabetes patients, thyroid glands of Hashimoto's thyroiditis, and gut of Crohn's disease patients, suggesting that such patients mount a TH1-like, not a TH2-like, response to the antigen(s) involved in the etiopathogenesis of such disorders.

A primary goal, for both diagnostic and therapeutic reasons, therefore, would be the ability to identify, isolate and/or target members of a particular TH cell subpopulation. The ability to identify those genes which are differentially expressed within and/or among such TH cell subpopulations is required to achieve such a goal. To date, investigations have focused on the expression of a limited number of specific known cytokines and cytokine receptors in the TH cell population. Cytokines, however, exert effects on cell types in addition to specific TH cell subpopulations, i.e., exhibit a variety of pleiotropic effects. It would be beneficial, therefore, to identify reliable markers (e.g., gene sequences) of TH cell subpopulations whose effects are TH cell subpopulation specific, e.g., which, unlike secreted cytokines, are TH cell subpopulation specific.

3. SUMMARY OF THE INVENTION

The present invention relates to the discovery, identification and characterization of nucleic acids that encode STIF, a novel protein differentially expressed within the TH2 cell subpopulation. The invention encompasses the following nucleotides, host cells expressing such nucleotides, and the expression products of such nucleotides: (a) nucleotides that encode mammalian STIFs, including the human STIF, and the STIF gene product; (b) nucleotides that encode portions of the STIF that correspond to its functional domains, and the polypeptide products specified by such nucleotide sequences; (c) nucleotides that encode mutants of the STIF in which all or a part of one of the domains is deleted or altered, and the polypeptide products specified by such nucleotide sequences; (d) nucleotides that encode fusion proteins containing the STIF or one of its domains fused to another polypeptide.

The invention also encompasses agonists and antagonists of STIF, including small molecules, large molecules, mutant STIF that competes with native natural STIF, and antibodies, as well as nucleotide sequences that can be used to inhibit STIF gene expression (e.g., antisense and ribozyme molecules, and gene or regulatory sequence replacement constructs) or to enhance STIF gene expression (e.g., expression constructs that place the STIF gene under the control of a strong promoter system), and transgenic animals that express an STIF transgene or "knock-outs" that do not express STIF.

Further, the present invention also relates to methods for the use of the STIF gene and/or STIF gene products for the identification of compounds which modulate, i.e., act as agonists or antagonists, of STIF gene expression and or STIF gene product activity.

The invention further provides methods for the identification of compounds which modulate the expression of the STIF gene or the activity of STIF gene product involved in STIF based disorders such as proliferative disorders or TH2 cell subpopulation-related disorders and processes relevant to the differentiation, maintenance and/or effector function of the subpopulations. Still further, the present invention provides methods for the treatment of STIF related disorders which can, for example, involve the administration of such modulatory compounds to individuals exhibiting STIF based disorders or TH cell subpopulation-related disorder symptoms or tendencies. Additionally, treatment can result in the stimulation or depletion of one or more of the TH cell subpopulations.

"Stimulation", as used herein, can refer to an effective increase in the number of cells belonging to the TH cell STIF expressing subpopulation, via, for example, the proliferation of such TH2 cell subpopulation cells. The term can also refer to an increase in the activity of cells belonging to the TH cell subpopulation, as would be evidenced, for example, by a per cell increase in the expression of the TH cell subpopulation-specific cytokine pattern. "Depletion", as used herein, can refer to an effective reduction in the number of cells belonging to a TH cell STIF expressing subpopulation, via, for example, a reduction in the proliferation of such TH cell subpopulation cells. The term can also refer to a decrease in the activity of cells belonging to a TH cell subpopulation, as would be evidenced, for example, by a per cell decrease in the expression of the TH cell subpopulation-specific cytokine pattern.

The invention further relates to methods of treating STIF related disorders, such as proliferative disorders, or immune disorders characterized by aberrant expression or activity of STIF. The methods of treatment involve the administration of compounds that act to modulate STIF expression or STIF activity. Such diseases include, but not limited to, cancer and chronic inflammatory diseases and disorders; such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

3.1 Definitions

As used herein, the following terms, whether used in the singular or plural, will have the meanings indicated:

STIF nucleotides or coding sequences means nucleotide sequences encoding STIF protein, polypeptide or peptide fragments of STIF protein, or STIF fusion proteins. STIF nucleotide sequences encompass DNA, including genomic DNA (e.g. the STIF gene) or cDNA, or RNA.

STIF: means natural STIF protein. Polypeptides or peptide fragments of STIF protein are referred to as STIF polypeptides or STIF peptides. Fusions of STIF, or STIF polypeptides or peptide fragments to an unrelated protein are referred to herein as STIF fusion proteins. A functional STIF refers to a protein which is differentially expressed within TH2 cells and is capable of regulating immune function.

4. DESCRIPTION OF THE FIGURES

FIGS. 1A–B. Nucleotide sequence (SEQ ID NO:1) and deduced amino acid sequence (SEQ ID NO:2) of murine STIF cDNA encoding murine STIF.

FIGS. 2A–C. Nucleotide sequence (SEQ ID NO:3) and deduced amino acid sequence (SEQ ID NO:4) of human STIF cDNA encoding human STIF.

FIG. 3. Nucleotide sequence (SEQ ID NO:5) and deduced amino acid sequence (SEQ ID NO:6) of human STIF cDNA encoding human STIF homlgue with sequence homology to MDA-7. This sequence is identical to MDA-7 except for an additional serine residue at amino acid position 15.

5. DETAILED DESCRIPTION OF THE INVENTION

STIF, described for the first time herein, is a novel protein differentially expressed within the TH2 cell subpopulation. The invention encompasses the use of STIF nucleotides, STIF proteins and peptides, as well as antibodies to the STIF (which can, for example, act as STIF agonists or antagonists), antagonists that inhibit STIF activity or expression, or agonists that activate STIF activity or increase its expression in the diagnosis and treatment of disorders, including, but not limited to treatment of STIF related disorders, such as proliferative disorders, or immune disorders. The diagnosis of an STIF abnormality in a patient, or an abnormality iii the STIF signal transduction pathway, will assist in devising a proper treatment or therapeutic regimen. In addition, STIF nucleotides and STIF proteins are useful for the identification of compounds effective in the treatment of disorders based on the aberrant expression or activity of the STIF.

In particular, the invention described in the subsections below encompasses STIF nucleotides, polypeptides or peptides corresponding to functional domains of the STIF, mutated, truncated or deleted STIFs, STIF fusion proteins (e.g., STIF protein or a functional domain of STIF, fused to an unrelated protein or peptide such as an immunoglobulin constant region, i.e., IgFc), nucleotide sequences encoding such products, and host cell expression systems that can produce such STIF products.

The invention also encompasses antibodies and anti-idiotypic antibodies (including Fab fragments), antagonists and agonists of the STIF, as well as compounds or nucleotide constructs that inhibit expression of the STIF gene (transcription factor inhibitors, antisense and ribozyme molecules, or gene or regulatory sequence replacement constructs), or promote expression of STIF (e.g., expression constructs in which STIF coding sequences are operatively associated with expression control elements such as promoters, promoter/enhancers, etc.). The invention also relates to host cells and animals genetically engineered to express the human STIF (or mutants thereof) or to inhibit or "knock-out" expression of the animal's endogenous STIF.

The STIF proteins or peptides, STIF fusion proteins, STIF nucleotide sequences, antibodies, antagonists and agonists can be useful for the detection of mutant STIFs or inappropriately expressed STIFs for the diagnosis of STIF related disorders including proliferative and immune disorders.

The invention relates to assays designed to screen for compounds or compositions that modulate STIF activity, i.e., compounds or compositions that act as agonists or antagonists of STIF, and thereby modulate STIF activity. To this end, cell-based assays or non-cell based assays can be used to detect compounds that interact with, e.g., bind to STIF. The cell-based assays have the advantage in that they can be used to identify compounds that affect STIF biological activity (i.e., signal transduction), including the identification for compounds that do not interact with STIF, but act on an intracellular component of the signal transduction pathway mediated by STIF.

The invention also relates to assays designed to screen for compounds or compositions that modulate STIF gene expression. For example, cell-based assays, or cell-lysate assays (e.g., in vitro transcription or translation assays) can be used to screen for compounds or compositions that modulate STIF transcription (e.g., compounds that modulate expression, production or activity of transcription factors involved in STIF gene expression; polynucleotides that form triple helical structures with a STIF regulatory region and inhibit transcription of the STIF gene, etc.). Alternatively, cell-based assays or cell-lysate assays can be used to screen for compounds or compositions that modulate translation of STIF transcriptions (e.g., antisense and ribozyme molecules).

Finally, the STIF protein products and fusion protein products, antibodies and anti-idiotypic antibodies (including Fab fragments), antagonists or agonists (including compounds that modulate signal transduction which may act on downstream targets in the STIF signal transduction pathway) can be used for therapy of STIF related disorders. Nucleotide constructs encoding functional STIFs, mutant STIFs, as well as antisense and ribozyme molecules can be used in "gene therapy" approaches for the modulation of STIF expression and/or activity in the treatment of STIF related disorders arising from the aberrant activity of the STIF.

5.1 Isolation of an Inducible TH2 Specific Gene Sequence

A variety of methods can be utilized for the identification of genes which are involved in STIF related disorder states, e.g., proliferation disorders, or TH cell subpopulation-related disorder states, and/or which are involved in differentiation, maintenance and/or effector function of the subpopulations.

In particular, such methods can be utilized for the identification of genes which are differentially expressed within and among TH cell subpopulations, including but not limited to TH1 and TH2 subpopulations. Such genes can be involved in, for example, TH cell subpopulation differentiation, maintenance, and/or effector function, and in TH cell subpopulation-related disorders. For example, TH cells can be induced to differentiate into either TH1 or TH2 states, can be stimulated with, for example, a foreign antigen, and can be collected at various points during the procedure for analysis of differential gene expression.

One such paradigm, referred to herein as a "T cell line paradigm", was utilized which used mature TH cell clones, such as TH1 and TH2 and TH1-like and TH2-like cell lines. Such TH cell lines also included the following well known murine cell lines: Doris, DAX, D1.1 and CDC25.

The TH cell clones can be stimulated in a variety of ways. Such stimulation methods include, but are not limited to, pharmacological methods, such as exposure to phorbol esters, calcium ionophores, or lectins (e.g., Concanavalin A), by treatment with antibodies directed against T-cell receptor epitopes (e.g., anti-CD3 antibodies) or exposure, in the presence of an appropriate antigen presenting cell (APC), to an antigen that the particular TH cells are known to recognize. Following such primary stimulation, the cells can be maintained in culture without stimulation and, for example, in the presence of IL-2, utilizing standard techniques well known to those of skill in the art. The cells can then be exposed to one or more additional cycles of stimulation and maintenance.

Cell samples can be collected during any point of such a procedure. For example, cells can be obtained following any stimulation period and/or any maintenance period. Additionally, cells can be collected during various points during the TH cell differentiation process. RNA collected from such samples can be compared and analyzed according to, for example, methods described, below, in Section 6.1. For example, RNA from TH0, TH1 and TH2 groups isolated at a given time point can then be analyzed and compared. Additionally, RNA from stimulated and non-stimulated cells within a given TH cell group can also be compared and analyzed. Further, RNA collected from undifferentiated TH cells can be compared to RNA collected from cells at various stages during the differentiative process which ultimately yields TH cell subpopulations.

In order to identify differentially expressed genes, RNA, either total or mRNA, can be isolated from the TH cells utilized in paradigms such as those described in Section 5.1.1.1. Any RNA isolation technique which does not select against the isolation of mRNA can be utilized for the purification of such RNA samples. See, for example, Ausubel, F. M. et al., eds., 1987–1993, *Current Protocols in Molecular Biology,* John Wiley & Sons, Inc. New York, which is incorporated herein by reference in its entirety. Additionally, large numbers of cell samples can readily be processed using techniques well known to those of skill in the art, such as, for example, the single-step RNA isolation process of Chomczynski, P. (1989, U.S. Pat. No. 4,843,155), which is incorporated herein by reference in its entirety.

Transcripts within the collected RNA samples which represent RNA produced by differentially expressed genes can be identified by utilizing a variety of methods which are well known to those of skill in the art. For example, differential screening (Tedder, T. F. et al., 1988, Proc. Natl. Acad. Sci. USA 85:208–212), subtractive hybridization (Hedrick, S. M. et al., 1984, Nature 308:149–153; Lee, S. W. et al., 1984, Proc. Natl. Acad. Sci. USA 88:2825), and, preferably, differential display (Liang, P. and Pardee, A. B., 1992, Science 257:967–971; U.S. Pat. No. 5,262,311, which are incorporated herein by reference in their entirety), can be utilized to identify nucleic acid sequences derived from genes that are differentially expressed.

Differential screening involves the duplicate screening of a cDNA library in which one copy of the library is screened with a total cell cDNA probe corresponding to the mRNA population of one cell type while a duplicate copy of the cDNA library is screened with a total cDNA probe corresponding to the MRNA population of a second cell type. For example, one cDNA probe can correspond to a total cell cDNA probe of a cell type or tissue derived from a control subject, while the second cDNA probe can correspond to a total cell cDNA probe of the same cell type or tissue derived from an experimental subject. Those clones which hybridize to one probe but not to the other potentially represent clones derived from genes differentially expressed in the cell type of interest in control versus experimental subjects.

Subtractive hybridization techniques generally involve the isolation of mRNA taken from two different sources, the hybridization of the MRNA or single-stranded cDNA reverse-transcribed from the isolated mRNA, and the removal of all hybridized, and therefore double-stranded, sequences. The remaining non-hybridized, single-stranded cDNAs, potentially represent clones derived from genes that are differentially expressed among the two MRNA sources. Such single-stranded cDNAs are then used as the starting material for the construction of a library comprising clones derived from differentially expressed genes.

The differential display technique is a procedure, utilizing the well-known polymerase chain reaction (PCR; the experimental embodiment set forth in Mullis, K. B., 1987, U.S. Pat. No. 4,683,202), which allows for the identification of sequences derived from genes which are differentially expressed. First, isolated RNA is reverse-transcribed into single-stranded cDNA, utilizing standard techniques which are well known to those of skill in the art. Primers for the reverse transcriptase reaction can include, but are not limited to, oligo dT-containing primers, preferably of the 3' primer type of oligonucleotide described below.

Next, this technique uses pairs of PCR primers, as described below, which allow for the amplification of clones representing a reproducible subset of the RNA transcripts present within any given cell. Utilizing different pairs of primers allows each of the primed mRNA transcripts present in a cell to be amplified. Among such amplified transcripts can be identified those which have been produced from differentially expressed genes.

The 3' oligonucleotide primer of the primer pairs can contain an oligo dT stretch of 10–13, preferably 11, dT nucleotides at its 5' end, which hybridizes to the poly(A) tail of mRNA or to the complement of a cDNA reverse transcribed from an mRNA poly(A) tail. In order to increase the specificity of the 3' primer, the primer can contain one or more, preferably two, additional nucleotides at its 3' end. Because, statistically, only a subset of the mRNA derived sequences present in the sample of interest will hybridize to such primers, the additional nucleotides allow the primers to amplify only a subset of the mRNA derived sequences present in the sample of interest. This is preferred in that it allows more accurate and complete visualization and characterization of each of the bands representing amplified sequences.

The 5' primer can contain a nucleotide sequence expected, statistically, to have the ability to hybridize to cDNA sequences derived from the cells or tissues of interest. The nucleotide sequence can be an arbitrary one, and the length of the 5' oligonucleotide primer can range from about 9 to about 15 nucleotides, with about 13 nucleotides being preferred.

Arbitrary primer sequences cause the lengths of the amplified partial cDNAs produced to be variable, thus allowing different clones to be separated by using standard denaturing sequencing gel electrophoresis.

PCR reaction conditions should be chosen which optimize amplified product yield and specificity, and, additionally, produce amplified products of lengths which can be resolved utilizing standard gel electrophoresis techniques. Such reaction conditions are well known to those of skill in the art, and important reaction parameters include, for example, length and nucleotide sequence of oligonucleotide primers as discussed above, and annealing and elongation step temperatures and reaction times.

The pattern of clones resulting from the reverse transcription and amplification of the mRNA of two different cell types is displayed via sequencing gel electrophoresis and compared. Differentially expressed genes are indicated by differences in the two banding patterns.

Once potentially differentially expressed gene sequences have been identified via bulk techniques such as, for example, those described above, the differential expression of such putatively differentially expressed genes should be corroborated. Corroboration can be accomplished via, for example, such well known techniques as Northern analysis, quantitative RT/PCR, or RNAse protection.

Upon corroboration, the differentially expressed genes can be further characterized, as discussed, below, in the Example section.

The amplified sequences of differentially expressed genes obtained through, for example, differential display can be used to isolate full length clones of the corresponding gene. The full length coding portion of the gene can readily be isolated, without undue experimentation, by molecular biological techniques well known in the art. For example, the isolated differentially expressed amplified fragment can be labeled and used to screen a cDNA library. Alternatively, the labeled fragment can be used to screen a geniomic library.

PCR technology can also be utilized to isolate full length cDNA sequences. As described, above, in this Section, the isolated, amplified gene fragments obtained through differential display have 5' terminal ends at some random point within the gene and usually have 3' termInal ends at a position corresponding to the 3' end of the transcribed portion of the gene. Once nucleotide sequence information from an amplified fragment is obtained, the remainder of the gene (i.e., the 5' end of the gene, when utilizing differential display) can be obtained using, for example, RT-PCR.

In one embodiment of such a procedure for the identification and cloning of full length gene sequences, RNA can be isolated, following standard procedures, from an appropriate tissue or cellular source. A reverse transcription reaction can then be performed on the RNA using an oligonucleotide primer complimentary to the mRNA that corresponds to the amplified fragment, for the priming of first strand synthesis. Because the primer is anti-parallel to the mRNA, extension will proceed toward the 5' end of the mRNA. The resulting RNA/DNA hybrid can then be "tailed" with guanines using a standard terminal transferase reaction, the hybrid can be digested with RNAase H, and second strand synthesis can then be primed with a poly-C primer. Using the two primers, the 5' portion of the gene is amplified using PCR. Sequences obtained can then be isolated and recombined with previously isolated sequences to generate a full-length cDNA of the differentially expressed genes of the invention. For a review of cloning strategies and recombinant DNA techniques, see e.g., Sambrook et al., 1989, Molecular Cloning, A Laboratory Manual, (Volumes 1–3) Cold Spring Harbor Press, N.Y.; and Ausubel et al., 1989, Current Protocols in Molecular Biology, Green Publishing Associates and Wiley Interscience, N.Y.

5.2 Characterization of the STIF TH2 Inducible Gene

The cDNA sequence (SEQ. ID. No. 1) and deduced amino acid sequence (SEQ. ID. No. 2) of the murine STIF are shown in FIGS. 1A–B. The cDNA sequence (SEQ. ID. NO. 3) and deduced amino acid sequence (SEQ. ID. NO. 4) of two human STIF genes are shown in FIGS. 2A–C and FIG. 3. The STIF nucleotide sequences of the invention include: (a) the DNA sequence shown in FIGS. 1A–B, FIGS. 2A–C or FIG. 3, contained in the murine or human cDNA clones as deposited with the American Type Culture Collection (ATCC; 10801 University Blvd., Manassas, Va. 20110-2209) and assigned Accession Nos. 98397 and 98427, respectively; (b) nucleotide sequences that encode the amino acid sequence shown in FIGS. 1A–B, FIGS. 2A–C, or FIG. 3 or the murine or human STIF amino acid sequences encoded by the cDNA clones as deposited with the ATCC and assigned Accession Nos. 98397 and 98427, respectively; (c) any nucleotide sequence that hybridizes to the complement of the DNA sequence shown in FIGS. 1A–B, FIGS. 2A–C, or FIG. 3 or contained in the murine or human cDNA clones as deposited with the ATCC and assigned Accession Nos. 98397 and 98427, respectively, under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3); (d) any nucleotide sequence that hybridizes to the complement of the DNA sequence shown in FIGS. 1A–B, FIGS. 2A–C or FIG. 3 or contained in the murine or human CDNA clones as deposited with the ATCC, and assigned Accession Nos. 98397 and 98427, respectively, under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° and encodes a functionally equivalent gene product; and (e) any nucleotide sequence that hybridizes to the complement of the DNA sequences that encode the amino acid sequence shown in FIGS. 1A–B, FIGS. 2A–C or FIG. 3, or contained in the murine or human cDNA clones as deposited with the ATCC and assigned Accession Nos. 98397 and 98427, respectively, under less stringent conditions, such as moderately stringent conditions, e.g., washing in 0.2×SSC/0.1% SDS at 42° C. (Ausubel et al., 1989, supra), and encodes a functionally equivalent STIF gene product. Functional equivalents of the STIF include naturally occurring STIF proteins present in other species, and mutant STIFs whether naturally occurring or engineered. The invention also includes degenerate variants of sequences (a) through (e).

Preferred STIF nucleic acids encode polypeptides that are at least 55% identical or similar to the amino acid sequence shown in FIGS. 1A–B, FIGS. 2A–C or FIG. 3 or the murine or human STIF amino acid sequence encoded by the cDNA clones as deposited with the ATCC and assigned Accession Nos. 98397 and 98427, respectively. Nucleic acids which encode polypeptides which are at least about 70%, and even more preferably at least about 80%, 85%, 90%, 95%, or 98% identical or similar with the amino acid sequence represented in FIGS. 1A–B, FIGS. 2A–C, or FIG. 3 or the murine or human STIF amino acid sequence encoded by the cDNA clones as deposited with the ATCC and assigned Accession Nos. 98397 and 98427, respectively, are also within the scope of the invention. In a particularly preferred embodiment, the nucleic acid of the present invention encodes a polypeptide having an overall amino acid sequence homology or identity of at least about 70%, at least about 80%, at least about 85%, at least about 90%, at least about 95%, at least about 98%, or at least 99% with the amino acid sequence shown in FIGS. 1A–B, FIGS. 2A–C, or FIG. 3, or the murine or human STIF amino acid sequence encoded by the cDNA clones as deposited with the ATCC and assigned Accession Nos. 98397 and 98427, repectively.

The invention also includes nucleic acid molecules, preferably DNA molecules, that hybridize to, and are therefore the complements of, the nucleotide sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6xSSC/ 0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as STIF antisense molecules, useful, for example, in STIF gene regulation (for and/or as antisense primers in amplification reactions of STIF gene nucleic acid sequences). With respect to STIF gene regulation, such techniques can be used to regulate, for example, STIF related disorders, such as proliferative, or immune disorders, e.g., cancer or TH cell related disorders. Further, such sequences may be used as part of ribozyme and/or triple helix sequences, also useful for STIF gene regulation.

In addition to the STIF nucleotide sequences described above, full length STIF cDNA or gene sequences present in the same species and/or homologs of the STIF gene present in other species can be identified and readily isolated, without undue experimentation, by molecular biological techniques well known in the art. The identification of homologs of STIF in related species can be useful for developing animal model systems more closely related to humans for purposes of drug discovery. For example, cDNA libraries, or genomic DNA libraries derived from the organism of interest can be screened by hybridization using the nucleotides described herein as hybridization or amplification probes. Furthermore, genes at other genetic loci within the genome that encode proteins which have extensive homology to one or more domains of the STIF gene product can also be identified via similar techniques. In the case of cDNA libraries, such screening techniques can identify clones derived from alternatively spliced transcripts in the same or different species.

Screening can be by filter hybridization, using duplicate filters. The labeled probe can contain at least 15–30 base pairs of the STIF nucleotide sequence, as shown in FIGS. 1A–B, FIGS. 2A–C or FIG. 3. The hybridization washing conditions used should be of a lower stringency when the cDNA library is derived from an organism different from the type of organism from which the labeled sequence was derived. With respect to the cloning of a STIF homolog, using murine or human STIF probes, for example, hybridization can, for example, be performed at 65° C. overnight in Church's buffer (7% SDS, 250 mM NaHPO$_4$, 2$\mu$M EDTA, 1% BSA). Washes can be done with 2xSSC, 0.1% SDS at 65° C. and then at 0.1xSSC, 0.1% SDS at 65° C.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Alternatively, the labeled STIF nucleotide probe may be used to screen a genomic library derived from the organism of interest, again, using appropriately stringent conditions. The identification and characterization of human genomic clones is helpful for designing diagnostic tests and clinical protocols for treating STIF based disorders in human patients. For example, sequences derived from regions adjacent to the intron/exon boundaries of the human gene can be used to design primers for use in amplification assays to detect mutations within the exons, introns, splice sites (e.g. splice acceptor and/or donor sites), etc., that can be used in diagnostics.

Further, an STIF gene homolog may be isolated from nucleic acid of the organism of interest by performing PCR using two degenerate oligonucleotide primer pools designed on the basis of amino acid sequences within the STIF gene product disclosed herein. The template for the reaction may be cDNA obtained by reverse transcription of mRNA prepared from, for example, cell lines or tissue, known or suspected to express an STIF gene allele.

The PCR product may be subcloned and sequenced to ensure that the amplified sequences represent the sequences of an STIF gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the STIF gene). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, CDNA sequences upstream of the amplified fragment may easily be isolated. For a review of cloning strategies which may be used, see e.g., Sambrook et al., 1989, supra.

The STIF gene sequences may additionally be used to isolate mutant STIF gene alleles. Such mutant alleles may be isolated from individuals either known or proposed to have a genotype which contributes to the symptoms of disorders arising from the aberrant expression or activity of the STIF protein. Mutant alleles and mutant allele products may then be utilized in the therapeutic and diagnostic systems described below. Additionally, such STIF gene sequences can be used to detect STIF gene regulatory (e.g., promoter or promotor/enhancer) defects which can affect the expression of the STIF.

A CDNA of a mutant STIF gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant STIF allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant STIF allele to that of the normal STIF allele, the mutation(s) responsible for the loss or alteration of function of the mutant STIF gene product can be ascertained.

Alternatively, a genomic library can be constructed using DNA obtained from an individual suspected of or known to carry the mutant STIF allele, or a cDNA library can be constructed using RNA from a tissue known, or suspected, to express the mutant STIF allele. The normal STIF gene or any suitable fragment thereof may then be labeled and used as a probe to identify the corresponding mutant STIF allele in such libraries. Clones containing the mutant STIF gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant STIF allele in an individual suspected of or known to carry such a mutant allele. In this manner, gene products made by the putatively mutant tissue may be expressed and screened using standard antibody screening techniques in conjunction with antibodies raised against the normal STIF gene product, as described, below, in Section 5.3. (For screening techniques, see, for example, Harlow, E. and Lane, eds., 1988, "Antibodies: A Laboratory Manual", Cold Spring Harbor Press, Cold Spring Harbor.) In cases where an STIr mutation results in an expressed gene product with altered function (e.g., as a result of a missense or a frameshift mutation), a polyclonal set of antibodies to STIF are likely to cross-react with the mutant STIF gene product. Library clones detected via their reaction with such labeled antibodies can be purified and subjected to sequence analysis according to methods well known to those of skill in the art.

The invention also encompasses nucleotide sequences that encode mutant STIFs, peptide fragments of the STIF, truncated STIFs, and STIF fusion proteins. These include, but are not limited to nucleotide sequences encoding mutant STIFs described in section 5.2 infra; polypeptides or peptides corresponding to one or more of the domains of the STIF protein or portions of these domains; truncated STIFs in which one or more of the domains is deleted, or a truncated, nonfunctional STIF lacking all, or a portion of a functional domain. Nucleotides encoding fusion proteins may include by are not limited to full length STIF, truncated STIF or peptide fragments of STIF fused to an unrelated protein or peptide, such as for example, a membrane sequence, which anchors the STIF to the cell membrane; an Ig Fc domain which increases the stability and half life of the resulting fusion protein (e.g., STIF-Ig) in the bloodstream; or an enzyme, fluorescent protein, luminescent protein which can be used as a marker.

The invention also encompasses (a) DNA vectors that contain any of the foregoing STIF coding sequences and/or their complements (i.e., antisense); (b) DNA expression vectors that contain any of the foregoing STIF coding sequences operatively associated with a regulatory element that directs the expression of the coding sequences; and (c) genetically engineered host cells that contain any of the foregoing STIF coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

5.3 STIF Proteins and Polypeptides

STIF protein, polypeptides and peptide fragments, mutated, truncated or deleted forms of the STIF and/or STIF fusion proteins can be prepared for a variety of uses, including but not limited to the generation of antibodies, as reagents in diagnostic assays, the identification of other cellular gene products involved in the regulation of the STIF signal translation pathway, as reagents in assays for screening for compounds that can be used in the treatment of STIF related disorders, and as pharmaceutical reagents useful in the treatment of disorders related to the STIF.

FIGS. 1A–B shows the amino acid sequence of a murine STIF protein. The STIF amino acid sequences of the invention include the amino acid sequence shown in FIGS. 1A–B (SEQ. ID. No:2). In addition, the invention encompasses STIF polypeptides which are at least about 70%, and even more preferably at least about 80%, 85%, 90%, 95%, or 98% identical or similar with the amino acid sequence represented in FIGS. 1A–B or the murine amino acid sequence encoded by the cDNA deposited with the ATCC and asigned accession no. 98397.

FIGS. 2A–C shows the amino acid sequence of a human STIF protein. The STIF amino acid sequences of the invention include the amino acid sequence shown in FIGS. 2A–C (SEQ. ID. No: 4). In addition, the invention encompasses STIF polypeptides which are at least about 70%, and even more preferably at least about 80%, 85%, 90%, 95%, or 98% identical or similar with the amino acid sequence represented in FIGS. 2A–C or the human amino acid sequence encoded by the cDNA deposited with the ATCC and assigned accession no. 98427.

In addition to the human STIF sequence shown in FIGS. 2A–C, an additional human STIF homologue was isolated that shared significant sequence homology with the human MDA-7 gene. The DA-7 DNA sequence differs from the human STIF sequence of FIG. 3 in that there is an additional serine residue at amino acid position 15.

The invention also encompasses proteins that are functionally equivalent to the STIF encoded by the nucleotide sequences described in Section 5.2, as judged by any of a number of criteria, including but not limited to TH2 specific gene expression, the ability to inhibit TH1 cell gamma interferon secretion and the ability to bind the natural STIF receptor resulting in the biological effect of natural STIF, e.g., signal transduction, a change in cellular metabolism (e.g., ion flux, tyrosine phosphorylation) or change in henotype when the STIF equivalent is present in an appropriate cell type. Such functionally equivalent STIF proteins include but are not limited to additions or substitutions of amino acid residues within the amino acid sequence encoded by the STIF nucleotide sequences described, above, in Section 5.2, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to STIF DNA (using random mutagenesis techniques well known to those skilled in the art) and the resulting mutant STIFs tested for activity, site-directed mutations of the STIF coding sequence can be engineered (using site-directed mutagenesis techniques well known to those skilled in the art) to generate mutant STIFs with increased function, e.g., higher binding affinity for natural STIF receptor, and/or greater signalling capacity; or decreased function, e.g., lower binding affinity for natural STIF receptor, and/or decreased signal transduction capacity.

For example, regions of identity may be determined by alignment of mouse STIF (FIGS. 1A–B) with the human STIF homologs (FIGS. 2A–C or FIG. 3). Mutant STIFs can be engineered so that regions of identity are maintained, whereas the variable residues are altered, e.g., by deletion or insertion of an amino acid residue(s) or by substitution of one or more different amino acid residues. Conservative alterations at the variable positions can be engineered in order to produce a mutant STIF that retains function; e.g., natural STIF receptor binding affinity or signal transduction capability or both. Non-conservative changes can be engineered at these variable positions to alter function, e.g., natural STIF receptor binding affinity or signal transduction capability, or both. Alternatively, where alteration of function is desired, deletion or non-conservative alterations of the conserved regions can be engineered. For example, deletion or non-conservative alterations of the of the mature STIF growth factor, amino acid residues of murine or human STIF, or amino acid residues, of the murine STIF (FIGS. 1A–B) or human STIF (FIGS. 2A–C and FIG. 3). Non-conservative alterations to STIF can be engineered to produce mutant STIFs with altered binding affinity for natural STIF receptor. The same mutation strategy can also be used to design mutant STIFs based on the alignment of murine and human STIF or STIF homologs from other species.

Other mutations to the STIF coding sequence can be made to generate STIFs that are better suited for expression, scale up, etc. in the host cells chosen. For example, cysteine residues can be deleted or substituted with another amino acid in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur in STIF (N-X-S or N-X-T), and/or an amino acid deletion at the second position of any one or more such recognition sequences in STIF will prevent glycosylation of the STIF at the modified tripeptide sequence. (See, e.g., Miyajima et al., 1986, EMBO J. 5(6):1193–1197).

Peptides corresponding to one or more domains of the STIF protein, truncated or deleted STIFs as well as fusion proteins in which the full length STIF, an STIF peptide or truncated STIF is fused to an unrelated protein are also within the scope of the invention and can be designed on the basis of the STIF nucleotide and STIF amino acid sequences disclosed in this Section and in Section 5.1, above. Such fusion proteins include but are not limited to IgFc fusions which stabilize the STIF protein or peptide and prolong half-life in vivo; or fusions to any amino acid sequence that allows the fusion protein to be anchored to the cell membrane, allowing STIF to be exhibited on the cell surface; or fusions to an enzyme, fluorescent protein, or luminescent protein which provide a marker function.

Such STIF polypeptides, peptides and fusion proteins can be produced by recombinant DNA technology using techniques well known in the art for expressing nucleic acid containing STIF gene sequences and/or coding sequences. A variety of methods can be used to construct expression vectors containing the STIF nucleotide sequences as described in Section 5.2 and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989., supra. Alternatively, RNA capable of encoding STIF nucleotide sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the STIF nucleotide sequences of the invention. Where the STIF peptide or polypeptide is a soluble derivative the peptide or polypeptide can be recovered from the culture, i.e., from the host cell in cases where the STIF peptide or polypeptide is not secreted, and from the culture media in cases where the STIF peptide or polypeptide is secreted by the cells. Purification or enrichment of the STIF from such expression systems can be accomplished using appropriate detergents and lipid micelles and methods well known to those skilled in the art.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing STIF nucleotide sequences; yeast (e.g., Saccharomyces, Pichia) transformed with recombinant yeast expression vectors containing the STIF nucleotide sequences; insect cell systems infected with recombinant virus expression vectors (e.g., baculovirus) containing the STIF sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing STIF nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression rectors may be advantageously selected depending upon the use intended for the STIF gene product being expressed. For example, when a large quantity of such a protein is to be produced, for the generation of pharmaceutical compositions of STIF protein or for raising antibodies to the STIF protein, for example, vectors which direct the expression of high levels of fusion protein products that are readily purified may be desirable. Such vectors include, but are not limited to the *E. coli* expression vector pUR278 (Ruther et al., 1983, EMBO J. 2:1791), in which the STIF coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiderda* cells. The STIF gene coding sequence may be cloned individually into non-essential regions (for example the polyhedrin gene) of the virus and placed under control of an AcNPV promoter (for example the polyhedrin promoter). Successful insertion of STIF gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the STIF nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the STIF gene product in infected hosts. (E.g., See Logan & Shenk, 1984, Proc. Natl. Acad. Sci. USA 81:3655–3659). Specific initiation signals may also be required for efficient translation of inserted STIF nucleotide sequences. These signals include the ATG initiation codon and adjacent sequences. In cases where an entire STIF gene or cDNA, including its own initiation codon and adjacent sequences, is inserted into the appropriate expression vector, no additional translational control signals may be needed. However, in cases where only a portion of the STIF coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3 and WI38.

For long-term, high-yield production of recombinant proteins, stable expression is preferred. For example, cell lines which stably express the STIF sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the STIF gene product. Such engineered cell lines may be particularly useful in screening and evaluation of compounds that affect the endogenous activity of the STIF gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

When used as a component in assay systems such as those described herein, the differentially expressed STIF gene protein can be labeled, either directly or indirectly, to facilitate detection of a complex formed between the STIF gene protein and a test substance. Any of a variety of suitable labeling systems can be used including but not limited to radioisotopes such as $^{125}I$; enzyme labelling systems that generate a detectable calorimetric signal or light when exposed to substrate; and fluorescent labels.

Indirect labeling involves the use of a protein, such as a labeled antibody, which specifically binds to the differentially expressed STIF gene. Such antibodies include but are not limited to polyclonal, monoclonal, chimeric, single chain, Fab fragments and fragments produced by an Fab expression library.

Where recombinant DNA technology is used to produce the STIF gene protein for such assay systems, it can be advantageous to engineer a fusion protein that can facilitate labeling (either direct or indirect), immobilization, solubility and/or detection.

Fusion proteins, which can facilitate solubility and/or expression, and can increase the blood half-life of the STIF protein, can include, but are not limited to soluble Ig-tailed fusion proteins. Methods for engineering such soluble Ig-tailed STIF fusion proteins are well known to those of skill in the art. See, for example U.S. Pat. No. 5,116,964, which is incorporated herein by reference in its entirety. Further, in addition to the Ig-region encoded by the IgG1 vector, the Fc portion of the Ig region utilized can be modified, by amino acid substitutions, to reduce complement activation and Fc binding. (See, e.g., European Patent No. 239400 B1, Aug. 3, 1994).

The STIF gene products can also be expressed in transgenic animals. Animals of any species, including, but not limited to, mice, rats, rabbits, guinea pigs, pigs, micro-pigs, goats, and non-human primates, e.g., baboons, monkeys, and chimpanzees may be used to generate STIF transgenic animals.

Any technique known in the art may be used to introduce the STIF transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the STIF transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the STIF gene transgene be integrated into the chromosomal site of the endogenous STIF gene, gene targeting is preferred. Briefly, when such a technique is to be utilized, vectors containing some nucleotide sequences homologous to the endogenous STIF gene are designed for the purpose of integrating, via homologous recombination with chromosomal sequences, into and disrupting the function of the nucleotide sequence of the endogenous STIF gene. The transgene may also be selectively introduced into a particular cell type, thus inactivating the endogenous STIF gene in only that cell type, by following, for example, the teaching of Gu et al. (Gu, et al., 1994, Science 265: 103–106). The regulatory sequences required for such a cell-type specific inactivation will depend upon the particular cell type of interest, and will be apparent to those of skill in the art.

Once transgenic animals have been generated, the expression of the recombinant STIF gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of STIF gene-expressing tissue, may also be evaluated immunocytochemically using antibodies specific for the STIF transgene product.

5.4 Antibodies to Differentially Expressed STIF Protein

Antibodies that specifically recognize one or more epitopes of STIF, or epitopes of conserved variants of STIF, or peptide fragments of the STIF are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention may be used, for example, in the detection of the STIF in a biological sample and may, therefore, be utilized as part of a diagnostic or prognostic technique whereby patients may be tested for abnormal amounts of STIF. Such antibodies may also be utilized in conjunction with, for example, compound screening schemes, as described, below, in Section 5.5, for the evaluation of the effect of test compounds on expression and/or activity of the STIF gene product. Additionally, such antibodies can be used in conjunction with the gene therapy techniques described, below, in Section 5.6, to, for example, evaluate the normal and/or engineered STIF-expressing cells prior to their introduction into the patient. Such antibodies may additionally be used as a method for the inhibition of abnormal STIF activity.

For the production of antibodies, various host animals may be immunized by injection with the STIF, an STIF peptide, truncated STIF polypeptides (STIF in which one or more domains have been deleted), functional equivalents of the STIF or mutants of the STIF. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.* Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody -s a molecule in which different portions are derived from different animal species, such as those having a variable region derived from a murine mAb and a human immunoglobulin constant region.

In addition, techniques have been developed for the production of humanized antibodies. (See, e.g., Queen, U.S. Pat. No. 5,585,089, which is incorporated herein by reference in its entirety.) An immunoglobulin light or heavy chain variable region consists of a "framework" region interrupted by three hypervariable regions, referred to as complementarily determining regions (CDRs). The extent of the framework region and CDRs have been precisely defined (see, "Sequences of Proteins of Immunological Interest", Kabat, E. et al., U.S. Department of Health and Human Services (1983). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against STIF gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989,.Science, 246:1275–1281) to allow rapid and easy identification of monoclonal Fab fragments with the desired specificity.

Antibodies to the STIF can, in turn, be utilized to generate anti-idiotype antibodies that "mimic" the STIF, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to STIF and competitively inhibit the binding of STIF to its cognate signaling receptor can be used to generate anti-idiotypes that "mimic" the STIF receptor and, therefore, bind and neutralize natural STIF. Such neutralizing anti-idiotypes or Fab fragments of such anti-idiotypes can be used in therapeutic regimens to neutralize the physiological activity of natural STIF.

5.5 Screening Assays for Compounds That Modulate STIF Expression or Activity The following assays are designed to identify compounds that are capable of modulating the expression or biological activity of STIF. Such compounds can be used to treat STIF related disorders arising from aberrant expression or activity of the STIF. Such diseases can include, for example, proliferative disorders or those associated with chronic inflammatory diseases and disorders, such as Crohn's disease, reactive arthritis, including Lyme disease, insulin-dependent diabetes, organ-specific autoimmunity, including multiple sclerosis, Hashimoto'thyroiditis and Grave's disease, contact dermatitis, psoriasis, graft rejection, graft verus host disease and sarcoidosis. TH2-like-related disorder symptoms can include, those associated with atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections including tuberculosis and lepromatous leprosy.

The following assays are designed to identify compounds that interact with (e.g., bind to) STIF, compounds that interfere with the interaction of STIF with its cognate signaling receptor involved in STIF-mediated signal transduction, and to compounds which modulate the activity of STIF gene (i.e., modulate the level of STIF gene expression) or modulate the level of STIF. Assays may additionally be utilized which identify compounds which bind to STIF gene regulatory sequences (e.g., promoter sequences) and which may modulate STIF gene expression. See e.g., Platt, K. A., 1994, J. Biol. Chem. 269:28558–28562, which is incorporated herein by reference in its entirety.

The compounds which may be screened in accordance with the invention include, but are not limited to peptides, antibodies and fragments thereof, and other organic compounds (e.g., peptidomimetics) that interact with (i.e., bind to) functional domains of the STIF protein. Peptides, antibodies or fragments thereof, and other organic compounds that mimic the STIF (or a portion thereof) which bind to and "neutralize" TH natural STIF cognate signaling receptor and thereby either mimic the activity triggered by the STIF cytokine (i.e., agonists) or inhibit the activity triggered by the STIF cytokine (i.e., antagonists) may also be screened in accordance with the invention.

Such compounds may include, but are not limited to, peptides such as, for example, soluble peptides, including but not limited to members of random peptide libraries; (see, e.g., Lam, K. S. et al., 1991, Nature 354:82–84; Houghten, R. et al., 1991, Nature 354:84–86), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al., 1993, Cell 72:767–778); molecules from natural product libraries, antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Other compounds which can be screened in accordance with the invention include but are not limited to small organic molecules that are able to gain entry into an appropriate cell and affect the expression of the STIF gene or some other gene involved in the STIF signal transduction pathway (e.g., by interacting with the regulatory region or transcription factors involved in gene expression); or such compounds that affect the activity of the natural STIF cognate signaling receptor or the activity of some other intracellular factor involved in the STIF signal transduction pathway.

5.5.1 Animal-and Cell-Based Model Systems

Described herein are cell- and animal-based systems which act as models for proliferative or immune disorders and for models of TH cell subpopulation differentiation, maintenance, and/or effector function. Cell- and animal-based model systems can also be used to further characterize the differentially expressed STIF gene. Such assays can be utilized as part of screening strategies designed to identify compounds which are capable of ameliorating STIF based disorders such as proliferative or TH cell subpopulation-related disorder symptoms. Thus, the animal- and cell-based models can be used to identify drugs, pharmaceuticals, therapies and interventions which can be effective in treating immune disorders such as TH cell subpopulation-related disorders that arise from aberrant expression or activity of the STIF cytokine. In addition, as described in detail, below, in Section 5.7.1, animal models can be used to determine the $LD_{50}$ and the $ED_{50}$ in animal subjects, and such data can be used to determine the in vivo efficacy of potential immune disorder treatments.

Animal-based model systems of STIF based disorders such as, but not limited to, TH cell subpopulation-related disorders, based on aberrant STIF expression or activity, can include both non-recombinant animals as well as recombinantly engineered transgenic animals.

Animal models for TH cell subpopulation-related disorders can include, for example, genetic models. For example, such animal models can include Leishmania resistance models, experimental allergic encephalomyelitis models and (BALB/c Cr×DBA/2Cr) F1 mice. These latter mice develop a fatal disseminated disease by systemic infection with virulent *Candida albicans* associated with strong TH2-like responses. Additionally, well known mouse models for asthma can be utilized to study the amelioration of symptoms caused by a TH2-like response. (See, for example, Lukacs, N. W. et al., 1994, Am. J. Resp. Cell Mol. Biol. 10:526–532; Gavett, S. H. et al., 1994, Am. J. Cell Mol. Biol. 10:587–593.) Further, the animal model, murine acquired immunodeficiency syndrome (MAIDS; Kanagawa, B. et al., 1993, Science 262:240; Makino, M. et al., 1990, J. Imm. 144:4347) can be used for such studies.

Alternatively, such well known animal models as SCIDhu mice (see for example, Kenshima, H. et al., 1994, Curr. Opin. Imm. 6327–333) which represents an in vivo model of the human hematolymphoid system, can be utilized. Further, the RAG-2-deficient blastocyst complementation technique (Chen, J. et al., 1993, Proc. Natl. Acad. Sci. USA 90:4528–4532; Shinkai, Y. et al., 1992, Cell 68:855–867) can be utilized to produce mice containing, for example, humanized lymphocytes and/or which express target gene sequences. Still further, targeting techniques directed specifically to T cells, for example, the technique of Gu et al. (Gu, H. et al., 1994, Science 265:103–106) can be utilized to produce animals containing transgenes in only T cell populations.

Animal models exhibiting STIF based disorder-like symptoms can be engineered by utilizing, for example, STIF sequences such as those described, above, in Section 5.2, in conjunction with techniques for producing transgenic animals that are well known to those of skill in the art. For example, STIF sequences can be introduced into, and overexpressed and/or misexpressed in, the genome of the animal of interest, or, if endogenous STIF sequences are present, they can either be overexpressed, misexpressed, or, alternatively, can be disrupted in order to underexpress or inactivate STIF gene expression.

In order to overexpress or misexpress a STIF gene sequence, the coding portion of the STIF gene sequence can be ligated to a regulatory sequence which is capable of driving high level gene expression or expression in a cell type in which the gene is not normally expressed in the animal and/or cell type of interest. Such regulatory regions will be well known to those of skill in the art, and can be utilized in the absence of undue experimentation.

For underexpression of an endogenous STIF gene sequence, such a sequence can be isolated and engineered such that when reintroduced into the genome of the animal of interest, the endogenous STIF gene alleles will be inactivated. Preferably, the engineered STIF gene sequence is introduced via gene targeting such that the endogenous STIF sequence is disrupted upon integration of the engineered STIF gene sequence into the animal's genome. Gene targeting is discussed, below, in this Section.

Animals of any species, including, but not limited to, mice, rats, rabbits, guinea pigs, pigs, micro-pigs, goats, and non-human primates, e.g., baboons, squirrels, monkeys, and chimpanzees can be used to generate animal models of TH cell subpopulation STIF-related disorders.

Any technique known in the art can be used to introduce a STIF transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the STIF transgene in all their cells, as well as animals which carry the transgene in some, but not all their cells, i.e., mosaic animals. (See, for example, techniques described by Jakobovits, 1994, Curr. Biol. 4:761–763.) The transgene can be integrated as a single transgene or in concatamers, e.g., head-to-head tandems or head-to-tail tandems. The transgene can also be selectively introduced into and activated in a particular cell type by following, for example, the teaching of Lasko et al. (Lasko, M. et al., 1992, Proc. Natl. Acad. Sci. USA 89:6232–6236). The regulatory sequences required for such a cell-type specific activation will depend upon the particular cell type of interest, and will be apparent to those of skill in the art.

When it is desired that the STIF transgene be integrated into the chromosomal site of the endogenous STIF gene, gene targeting is preferred. Briefly, when such a technique is to be utilized, vectors containing some nucleotide sequences homologous to the endogenous STIF gene of interest are designed for the purpose of integrating, via homologous recombination with chromosomal sequences, into and disrupting the function of, the nucleotide sequence of the endogenous STIF gene. The transgene can also be selectively introduced into a particular cell type, thus inactivating the endogenous gene of interest in only that cell type, by following, for example, the teaching of Gu et al. (Gu, H. et al., 1994, Science 265:103–106). The regulatory sequences required for such a cell-type specific inactivation will depend upon the particular cell type of interest, and will be apparent to those of skill in the art.

Once transgenic animals have been generated, the expression of the recombinant STIF gene and protein can be assayed utilizing standard techniques. Initial screening can be accomplished by Southern blot analysis or PCR techniques to analyze animal tissues to assay whether integration of the transgene has taken place. The level of mRNA expression of the STIF transgene in the tissues of the transgenic animals can also be assessed using techniques which include but are not limited to Northern blot analysis of tissue samples obtained from the animal, in situ hybridization analysis, and RT-PCR. Samples of target gene-expressing tissue, can also be evaluated immunocytochemically using antibodies specific for the target gene transgene gene product of interest.

The STIF transgenic animals that express STIF gene mRNA or STIF transgene peptide (detected immunocytochemically, using antibodies directed against target gene product epitopes) at easily detectable levels can then be further evaluated to identify those animals which display characteristic STIF based disorder symtoms such as proliferative or TH cell subpopulation-related disorder-like symptoms, or exhibit characteristic TH cell subpopulation differentiation phenotypes. TH2-like-related disorder symptoms can include, for example, those associated with chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease and sarcoidosis. TH2-like-related disorder symptoms can include, those associated with atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

Additionally, specific cell types within the transgenic animals can be analyzed and assayed for cellular phenotypes characteristic of TH cell subpopulation-related disorders. Such cellular phenotypes can include, for example, differential cytokine expression characteristic of the TH cell subpopulation of interest. Further, such cellular phenotypes can include an assessment of a particular cell type's fingerprint pattern of expression and its comparison to known fingerprint expression profiles of the particular cell type in animals exhibiting specific TH cell subpopulation-related disorders. Such transgenic animals serve as suitable model systems for TH cell-related disorders.

Once STIF transgenic founder animals are produced (i.e., those animals which express STIF proteins in cells or tissues of interest, and which, preferably, exhibit symptoms of STIF based disorders), they can be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound STIF transgenics that express the STIF transgene of interest at higher levels because of the effects of additive expression of each STIF transgene; crossing of heterozygous transgenic animals to produce animals homozygous for a given integration site in order to both augment expression and eliminate the possible need for screening of animals by DNA analysis; crossing of separate homozygous lines to produce compound heterozygous or homozygous lines; breeding animals to different inbred genetic backgrounds so as to examine effects of modifying alleles on expression of the STIF transgene and the development of TH cell subpopulation-related disorder-like symptoms. One such approach is to cross the STIF transgenic founder animals with a wild type strain to produce an F1 generation that exhibits TH cell subpopulation-related disorder-like symptoms, such as those described above. The F1 generation can then be inbred in order to develop a homozygous line, if it is found that homozygous target gene transgenic animals are viable.

Cells that contain and express STIF sequences which encode STIF protein, and, further, exhibit cellular phenotypes associated with a STIF based disorder, such as a TH cell subpopulation-related disorder of interest, can be utilized to identify compounds that exhibit an ability to ameliorate TH cell subpopulation-related disorder symptoms. Cellular phenotypes which can indicate an ability to ameliorate TH cell subpopulation-related disorder symptoms can include, for example, an inhibition or potentiation of STIF expression associated with the TH cell subpopulation of interest, or, alternatively, an inhibition or potentiation of specific TH cell subpopulations.

Further, the fingerprint pattern of gene expression of cells of interest can be analyzed and compared to the normal, non-TH cell subpopulation-related disorder fingerprint pattern. Those compounds which cause cells exhibiting TH cell subpopulation-related disorder-like cellular phenotypes to produce a fingerprint pattern more closely resembling a normal fingerprint pattern for the cell of interest can be considered candidates for further testing regarding an ability to ameliorate TH cell subpopulation-related disorder symptoms.

Cells which can be utilized for such assays can, for example, include non-recombinant cell lines, such as Dorris, AE7, D10.G4, DAX, D1.1 and CDC25 cell lines. In addition, purified primary naive T cells derived from either transgenic or non-transgenic strains can also be used.

Further, cells which can be used for such assays can also include recombinant, transgenic cell lines. For example, the TH cell subpopulation-related disorder animal models of the invention, discussed, above, can be used to generate, for example, TH1-like and/or TH2-like cell lines that can be used as cell culture models for the disorder of interest. While primary cultures derived from TH cell subpopulation-related disorder transgenic animals can be utilized, the generation of continuous cell lines is preferred. For examples of techniques which can be used to derive a continuous cell line from the transgenic animals, see Small et al., 1985, Mol. Cell Biol. 5:642–648.

Assays may also be developed which take advantage of the fact that certain cell types respond to STIF by either stimulation, or inhibition, of cytokine production. Screening for such cells may be facilitated through the use of a cytosensor microphysiometer such as that described in McConnell et al. (1992, Science 257:1906). The macrophysiometer can be used to detect and monitor the ability of cells to respond to STIF gene product. For example, assays may be designed to screen for compounds that modulate STIF induced stimulation, or inhibition, of cytokine production. Such assays may utilize monocytes that respond to STIF by secretion of cytokines, including but not limited to, IL-1α, IL-1β, IL-6, IL-8, TNF-α, GM-CSF and G-CSF. The STIF induced modulation of cytokine production can be assayed using methods well known to those skilled in the art, including cytokine specific ELISA assays. While primary monocyte cultures may be used in such assays, monocyte cell lines such as THP-1 (ATCC TIB 202) may also be used. Alternatively, any cell type that produces cytokines in response to STIF may be used to screen for compounds that modulate that response.

Further, cells of a cell type known to be involved in TH cell subpopulation-related disorders can be transfected with sequences capable of increasing or decreasing the amount of STIF gene expression within the cell. For example, STIF gene sequences can be introduced into, and overexpressed in, the genome of the cell of interest, or, if endogenous STIF gene sequences are present, they can either be overexpressed or, alternatively, can be disrupted in order to underexpress or inactivate STIF gene expression.

In order to overexpress a STIF gene sequence, the coding portion of the STIF gene sequence can be ligated to a regulatory sequence which is capable of driving gene expression in the cell type of interest. Such regulatory regions will be well known to those of skill in the art, and can be utilized in the absence of undue experimentation.

For underexpression of STIF gene sequence, such a STIF sequence can be isolated and engineered such that when reintroduced into the genome of the cell type of interest, the endogenous STIF gene alleles will be inactivated. Preferably, the engineered STIF gene sequence is introduced via gene targeting such that the endogenous STIF sequence is disrupted upon integration of the engineered STIF gene sequence into the cell's genome. Gene targeting is discussed, above.

Transfection of STIF gene sequence nucleic acid can be accomplished by utilizing standard techniques. See, for example, Ausubel, 1989, supra. Transfected cells should be evaluated for the presence of the recombinant STIF gene sequences, for expression and accumulation of STIF gene mRNA, and for the presence of recombinant STIF gene protein production. In instances wherein a decrease in STIF gene expression is desired, standard techniques can be used to demonstrate whether a decrease in endogenous STIF gene expression and/or in STIF gene product production is achieved.

The following assays are designed to identify compounds that bind to STIF gene products, bind to other cellular proteins that interact with a STIF gene product, and to compounds that interfere with the interaction of the STIF gene product with other cellular proteins.

Compounds can include, but are not limited to, other cellular proteins. Further, such compounds can include, but are not limited to, peptides such as, for example, soluble peptides, including, but not limited to, Ig-tailed fusion peptides and members of random peptide libraries (see, e.g., Lam, K. S. et al., 1991, Nature 354:82–84; Houghten, R. et al., 1991, Nature 354:84–86) made of D-and/or L-configuration amino acids, phosphopeptides (including but not limited to members of random or partially degenerate, directed phosphopeptide libraries; see, e.g., Songyang, Z. et al., 1993, Cell 72:767–778), antibodies (including, but not limited to polyclonal, monoclonal, humanized, anti-idiotypic, chimeric or single chain antibodies, and FAb, $F(ab')_2$ and FAb expression library fragments, and epitope-binding fragments thereof), and small organic or inorganic molecules.

Computer modelling and searching technologies permit identification of compounds, or the improvement of already identified compounds, that can modulate STIF gene expression or activity. Having identified such a compound or composition, the active sites or regions are identified.

In the case of compounds affecting receptor/STIF interactions, such active sites might typically be receptor binding sites, such as the interaction domains of STIF with its cognate signaling receptor. The active site can be identified using methods known in the art including, for example, from the amino acid sequences of peptides, from the nucleotide sequences of nucleic acids, or from study of complexes of the relevant compound or composition with its natural receptor. In the latter case, chemical or X-ray crystallographic methods can be used to find the active site by finding where on the factor the complexed receptor is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modelling can be used to complete the structure or improve its accuracy. Any recognized modelling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential target or pathway gene product modulating compounds.

Alternatively, these methods can be used to identify improved modulating compounds from an already known modulating compound. The composition of the known compound can be modified and the structural effects of modification can be determined using the experimental and computer modelling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds of improved specificity or activity.

Further experimental and computer modeling methods useful to identify modulating compounds based upon identification of the active sites of target or pathway gene or gene products and related transduction and transcription factors will be apparent to those of skill in the art.

Examples of molecular modelling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modelling of drugs interactive with specific proteins, such as Rotivinen, et al., 1988, *Acta Pharmaceutical Fennica* 97:159–166; Ripka, *New Scientist* 54–57 (Jun. 16, 1988); McKinaly and Rossmann, 1989, *Annu. Rev. Pharmacol. Toxiciol.* 29:111–122; Perry and Davies, *OSAR: Quantitative Structure-Activity Relationships in Drug Design* pp. 189–193 (Alan R. Liss, Inc. 1989); Lewis and Dean, 1989 Proc. R. Soc. Lond. 236:125–140 and 141–162; and, with respect to a model receptor for nucleic acid components, Askew, et al., 1989, *J. Am. Chem. Soc.* 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although generally described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein can be useful, for example, in elaborating the biological function of the STIF gene product, and for ameliorating the symptoms of STIF based disorders based on aberrant STIF expression or activity. In instances, for example, in which a proliferative or a TH cell subpopulation-related disorder situation results from a lower overall level of STIF gene expression, STIF gene product, and/or STIF gene product activity in a cell or tissue involved in such a disorder, compounds that interact with the STIF gene product can include ones which accentuate or amplify the activity of the bound STIF gene protein. Such compounds would bring about an effective increase in the level of STIF gene activity, thus ameliorating symptoms. In instances whereby mutations within the STIF gene cause aberrant STIF gene proteins to be made which have a deleterious effect or regulation of cellular proliferation or that leads to a TH cell subpopulation-related disorder, or, alternatively, in instances whereby normal STIF gene activity is necessary for a TH cell subpopulation-related disorder to occur, compounds that bind STIF gene protein can be identified that inhibit the activity of the bound STIF gene protein. Assays for identifying additional compounds as well as for testing the effectiveness of compounds, identified by, for example, techniques, such as those described in Section 5.5.2–5.5.3 are discussed, below.

5.5.2 In Vitro Screening Assays for Compounds That Bind to STIF

In vitro systems may be designed to identify compounds capable of interacting with (e.g., binding to) STIF. Compounds identified may be useful, for example, in modulating the activity of wild type and/or mutant STIF gene products; may be useful in elaborating the biological function of the STIF; may be utilized in screens for identifying compounds that disrupt normal STIF interactions; or may in themselves disrupt such interactions.

The principle of the assays used to identify compounds that bind to the STIF involves preparing a reaction mixture of the STIF and the test compound under conditions and for a time sufficient to allow the two components to interact and bind, thus forming a complex which can be removed and/or detected in the reaction mixture. The STIF species used can vary depending upon the goal of the screening assay. For example, where agonists of the natural STIF are sought, the full length STIF can be utilized.

The screening assays can be conducted in a variety of ways. For example, one method to conduct such an assay would involve anchoring the STIF protein, polypeptide, peptide or fusion protein or the test substance onto a solid phase and detecting STIF/test compound complexes anchored on the solid phase at the end of the reaction. In one embodiment of such a method, the STIF reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for STIF protein, polypeptide, peptide or fusion protein or the test compound to anchor any complexes formed in solution, and a labeled antibody specific for the other component of the possible complex to detect anchored complexes.

In yet another embodiment of the invention Real Time BIA (Biomolecular Interaction Analysis) from Pharmacia Biosensor AB may be utilized to monitor the ability of a given compound to interact with the STIF gene product. Once compounds are identified based on their ability to bind STIF the BIA may be used to determine the affinity, kinetics and cooperativity in binding.

The STIF gene product of the invention can, in vivo, interact with one or more cellular or extracellular macromolecules, such as proteins. Such macromolecules can include, but are not limited to, nucleic acid molecules and those proteins identified via methods such as those described, above, in Section 5.8.2. For purposes of this discussion, such cellular and extracellular macromolecules are referred to herein as "binding partners". Compounds that disrupt such interactions can be useful in regulating the activity of the STIF gene protein, especially mutant STIF gene proteins. Such compounds can include, but are not limited to molecules such as antibodies, peptides, and the like, as described, for example, in Section 5.5.1. above.

The basic principle of the assay systems used to identify compounds that interfere with the interaction between the STIF gene product and its cellular or extracellular binding partner or partners involves preparing a reaction mixture containing the STIF gene product and the binding partner under conditions and for a time sufficient to allow the two to interact and bind, thus form a complex. In order to test a compound for inhibitory activity, the reaction mixture is prepared in the presence and absence of the test compound. The test compound can be initially included in the reaction mixture, or can be added at a time subsequent to the addition of STIF gene product and its cellular or extracellular binding partner. Control reaction mixtures are incubated without the test compound or with a placebo. The formation of any complexes between the STIF gene protein and the cellular or extracellular binding partner is then detected. The formation of a complex in the control reaction, but not in the reaction mixture containing the test compound, indicates that the compound interferes with the interaction of the STIF gene protein and the interactive binding partner. Additionally, complex formation within reaction mixtures containing the test compound and normal STIF gene protein can also be compared to complex formation within reaction mixtures containing the test compound and a mutant STIF gene protein. This comparison can be important in those cases wherein it is desirable to identify compounds that disrupt interactions of mutant but not normal STIF gene proteins.

The assay for compounds that interfere with the interaction of the STIF gene products and binding partners can be conducted in a heterogeneous or homogeneous format. Heterogeneous assays involve anchoring either the STIF gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the STIF gene products and the binding partners, e.g., by competition, can be identified by conducting the reaction in the presence of the test substance; i.e., by adding the test substance to the reaction mixture prior to or simultaneously with the STIF gene protein and interactive cellular or extracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the STIF gene protein or the interactive cellular or extracellular binding partner, is anchored onto a solid surface, while the non-anchored species is labeled, either directly or indirectly. In practice, microtiter plates are conveniently utilized. The anchored species can be immobilized by non-covalent or covalent attachments. Non-covalent attachment can be accomplished simply by coating the solid surface with a solution of the STIF gene product or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (The antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the STIF gene protein and the interactive cellular or extracellular binding partner is prepared in which either the STIF gene product or its binding partner is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt STIF gene protein/cellular or extracellular binding partner interaction can be identified.

In a particular embodiment, the STIF gene product can be prepared for immobilization using recombinant DNA techniques described in Section 5.5, above. For example, the STIF gene coding region can be fused to a glutathione-S-transferase (GST) gene using a fusion vector, such as pGEX-5X-1, in such a manner that its binding activity is maintained in the resulting fusion protein. The interactive cellular or extracellular binding partner can be purified and used to raise a monoclonal antibody, using methods routinely practiced in the art and described above, in Section 5.6. This antibody can be labeled with the radioactive isotope $^{125}$I, for example, by methods routinely practiced in the art. In a heterogeneous assay, e.g., the GST-STIF gene fusion protein can be anchored to glutathione-agarose beads. The interactive cellular or extracellular binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the STIF gene protein and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-STIF gene fusion protein and the interactive cellular or extracellular binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the STIF gene product/binding partner interaction can be detected by adding the labeled antibody and measuring the radioactivity associated with the beads.

In another embodiment of the invention, these same techniques can be employed using peptide fragments that correspond to the binding domains of the STIF gene product and/or the interactive cellular or extracellular binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the cellular or extracellular binding partner is obtained, short gene segments can be engineered to express peptide fragments of the protein, which can then be tested for binding activity and purified or synthesized.

For example, and not by way of limitation, a STIF gene product can be anchored to a solid material as described, above, in this Section, by making a GST-STIF gene fusion protein and allowing it to bind to glutathione agarose beads. The interactive cellular or extracellular binding partner can be labeled with a radioactive isotope, such as $^{35}$S, and cleaved with a proteolytic enzyme such as trypsin. Cleavage products can then be added to the anchored GST-STIF gene fusion protein and allowed to bind. After washing away unbound peptides, labeled bound material, representing the cellular or extracellular binding partner binding domain, can be eluted, purified, and analyzed for amino acid sequence by well known methods. Peptides so identified can be produced synthetically or fused to appropriate facilitative proteins using well known recombinant DNA technology.

5.5.3 Assays for Identification of Compounds That Ameliorate STIF Related Disorders Compounds, including but not limited to binding compounds identified via assay techniques such as those described, above, in Sections 5.5.1 through 5.5.3, can be tested for the ability to ameliorate STIF related disorder symptoms, including proliferative disorders such as cancer, or immune disorder symptoms, including but not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

The assays described above can identify compounds which affect STIF activity (e.g., compounds that bind to the STIF, inhibit binding to the natural cognate signaling receptor, and either activate signal transduction (agonists) or block activation (antagonists), and compounds that bind to the natural receptor of STIF and neutralize activity); or compounds that affect STIF gene activity (by affecting STIF gene expression, including molecules, e.g., proteins or small organic molecules, that affect or interfere with splicing events so that expression of the full length or the truncated form of the STIF can be modulated). However, it should be noted that the assays described can also identify compounds that modulate STIF signal transduction (e.g., compounds which affect downstream signalling events, such as inhibitors or enhancers of G-protein activities which participate in transducing the signal activated by natural STIF receptor binding to the STIF). The identification and use of such compounds which affect another step in the STIF signal transduction pathway in which the STIF gene and/or STIF gene product is involved and, by affecting this same pathway may modulate the effect of STIF on the development of disorders that are within the scope of the invention. Such compounds can be used as part of a therapeutic method for the treatment of STIF related disorders, such as proliferative disorders, or immune disorders.

The invention encompasses cell-based and animal model-based assays for the identification of compounds exhibiting such an ability to ameliorate disorder symptoms.

Cell-based systems can be used to identify compounds which may act to ameliorate STIF based disorder symptoms.

Such cell systems can include, for example, recombinant or non-recombinant cells, such as cell lines, which express the STIF gene. In addition, expression host cells (e.g., COS cells, CHO cells, fibroblasts) genetically engineered to express a functional STIF receptor and to respond to activation by the natural STIF, e.g., as measured by a chemical or phenotypic change, induction of another host cell gene, change in ion flux (eg., $Ca^{++}$), inositol phosphate levels, tyrosine phosphorylation of host cell proteins, etc., can be used as an end point in the assay.

In accordance with the invention, a cell-based assay system can be used to screen for compounds that modulate the activity of STIF, i.e., agonists or antagonists; and thereby, modulate STIF based disorders. Host cells that respond to activation by STIF peptides can be used as an endpoint in the assay; e.g., as measured by a chemical, physiological, biological, or phenotypic change, regulation of proliferation, induction or inhibition of cytokine production, induction of a host cell gene or a reporter gene, change in cAMP levels, adenylyl cyclase activity, host cell G protein activity, extracellular acidification rate, host cell kinase activity, proliferation, differentiation, etc. To be useful in screening assays, such host cells should give a significant response to STIF, preferably greater than 5-fold induction over background.

In utilizing such cell based assay systems, the host cells that respond to activation by STIF are exposed to a test compound or to vehicle controls (e.g., placebos). After exposure, the cells can be assayed to measure the expression and/or activity of components of the signal transduction pathway of STIF, or the activity of the signal transduction pathway itself can be assayed. For example, after exposure, cells can be assayed for stimulation of proliferation, or alternatively, cell lysates may be assayed for cytokine production. Alternatively, in screening for compounds that may act as antagonists of STIF, it is necessary to test for inhibition of signal transduction by the test compound as compared to vehicle controls.

In utilizing such cell systems, cells may be exposed to a compound suspected of exhibiting an ability to ameliorate STIF disorder symptoms, at a sufficient concentration and for a time sufficient to elicit suppression of disorder symptoms in the exposed cells. After exposure, the cells can be assayed to measure alterations in the expression of the STIF gene, e.g., by assaying cell lysates for STIF mRNA transcripts (e.g., by Northern analysis) or for STIF protein expressed in the cell; compounds which regulate or modulate expression of the STIF gene are good candidates as therapeutics. Still further, the expression and/or activity of components of the signal transduction pathway of which STIF is a part, or the activity of the STIF signal transduction pathway itself can be assayed.

In addition, animal-based STIF based disorders systems, may be used to identify compounds capable of ameliorating disorder-like symptoms. Animal based screening methods may include, but are to be limited to, assays designed to measure an immunological response to antigen stimulation (such as ovalbumin (OVA) stimulation. Such responses may include production of an antibody response, stimulation or inhibition of cytokine production and/or measurement of eosinophil infiltration.

Such animal models may be used as test substrates for the identification of drugs, pharmaceuticals, therapies and interventions which may be effective in treating such disorders. For example, animal models may be exposed to a compound, suspected of exhibiting an ability to ameliorate disorder symptoms, at a sufficient concentration and for a time sufficient to elicit such an amelioration of body symptoms in the exposed animals. The response of the animals to the exposure may be monitored by assessing the reversal of STIF based disorders, such as proliferative disorders, or immune disorders. With regard to intervention, any treatments which reverse any aspect of disorder-like symptoms should be considered as candidates for human therapeutic intervention. Dosages of test agents may be determined by deriving dose-response curves, as discussed in Section 5.7.1, below.

5.6. The Treatment of STIF Based Disorders

The invention encompasses methods and compositions for treating STIF based disorders, including but not limited to proliferative disorders such as cancer, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

Symptoms of certain STIF based disorders may be ameliorated by decreasing the level of STIF gene expression, and/or STIF gene activity, and/or downregulating activity of the STIF pathway (e.g., by targeting downstream signalling events). Different approaches are discussed below.

Described below are methods and compositions which can be used to ameliorate STIF disorder symptoms via, for example, a modulation cell proliferative, or of the TH cell subpopulation of interest. Such modulation can be of a positive or negative nature, depending on the specific situation involved, but each modulatory event yields a net result in which symptoms of the STIF based disorder are ameliorated. Further, described below are methods for the modulation of TH cell responsiveness to antigen.

"Negative modulation", as used herein, refers to a reduction in the level and/or activity of STIF gene product relative to the level and/or activity of the STIF gene product in the absence of the modulatory treatment. Alternatively, the term, as used herein, refers to a depletion of the T cell subpopulation (e.g., via a reduction in the number of cells belonging to the TH cell subpopulation) relative to the number present in the absence of the modulatory treatment.

"Positive modulation", as used herein, refers to an increase in the level and/or activity of STIF gene product relative to the level and/or activity of the gene product in the absence of the modulatory treatment. Alternatively, the term, as used herein, refers to a stimulation of the T cell subpopulation (e.g., via an increase in the number of cells belonging to the TH cell subpopulation), relative to the number present in the absence of the modulatory treatment.

It is possible that a TH cell subpopulation-related disorder or other immune disorder, can occur as a result of normal STIF gene activity during the course of, for example, exposure to a certain antigen which elicits an immune response that leads to the development of the disorder. For example, the TH2-like-related disorders, asthma and allergy, are likely candidates of disorders having such a mechanism. Additionally, a disorder can be brought about, at least in part, by an abnormally high level of STIF gene product, or by the presence of a STIF gene product exhibiting an abnormal activity. As such, a technique which elicits a negative modulatory effect, i.e., brings about a reduction in the level and/or activity of STIF gene product, or alternatively, brings about a depletion of the TH cell subpopulation (e.g., via a physical reduction in the number of cells belonging to the TH cell subpopulation), would effect an amelioration of TH cell subpopulation-related disorder symptoms in either of the above scenarios.

Negative modulatory techniques for the reduction of STIF gene expression levels or STIF gene product activity levels, (either normal or abnormal), and for the reduction in the number of specific TH cell subpopulation cells are discussed below.

Alternatively, it is possible that a TH cell subpopulation-related disorder or other immune disorders can be brought about, at least in part, by the absence or reduction of the level of STIF gene expression, a reduction in the level of a STIF gene product's activity, or a reduction in the overall number of cells belonging to a specific TH cell subpopulation. As such, a technique which elicits a positive modulatory effect, i.e., brings about an increase in the level of STIF gene expression and/or the activity of such gene products, or, alternatively, a stimulation of the TH cell subpopulation (e.g., via a physical increase in the number of cells belonging to a TH cell subpopulation), would effect an amelioration of immune disorder symptoms.

For example, a reduction in the overall number of TH1-like cells relative to TH2-like cells within a HIV-infected individual can correlate with the progression to AIDS (Clerci, M. et al., 1993, J. Clin. Invest. 91:759; Clerci, M. et al., 1993, Science 262:1721; Maggi, E. et al., 1994, Science 265:244). A treatment capable of increasing the number of TH1-like cells relative to TH2-like cells within an HIV-infected individual may, therefore, serve to prevent or slow the progression to disease.

Positive modulatory techniques for increasing STIF gene expression levels or STIF gene product activity levels, and for increasing the level of specific TH cell subpopulation cells are discussed below.

Among the immune disorders whose symptoms can be ameliorated are TH1 or TH1-like related immune disorders and TH2 or TH2-like related immune disorders. Examples of TH1 or TH1-like related disorders include chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease and sarcoidosis. Examples of TH2 or TH2-like related disorders include atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

The methods described herein can additionally be utilized the modulate the level of responsiveness, for example, responsiveness to antigen, of a TH cell subpopulation. Such methods are important in that many immune disorders involve inappropriate rather than insufficient immune responses. For example, disorders such as atopic, IgE-mediated allergic conditions, including asthma, pathogen susceptibilities and chronic inflammatory disease, involve strong but counterproductive TH2-mediated immune responses. Further, inappropriate TH1-mediated immune responses to self-antigens is central to the development of such disorders as multiple sclerosis, psoriasis, insulin dependent diabetes, Hashimoto's thyroiditis and Crohn's disease.

Methods for modulating TH cell responsiveness can comprise, for example, contacting a compound to a TH cell so that the responsiveness of the T helper cell is modulated relative to the responsiveness of the T helper cell in the absence of the compound. The modulation can increase or decrease the responsiveness of the TH cell. Any of the techniques described, below, in Sections 5.7 can be utilized to effect an appropriate modulation of TH cell responsiveness.

As discussed, above, successful treatment of certain immune disorders can be brought about by techniques which serve to inhibit the expression or activity of STIF gene products, or which, alternatively, serve to reduce the overall number of cells belonging to a specific TH cell subpopulation.

For example, compounds such as those identified through assays described, above, in Section 5.3, which exhibit negative modulatory activity, can be used in accordance with the invention to ameliorate certain TH cell subpopulation-related disorder symptoms. As discussed in Section 5.3, above, such molecules can include, but are not limited to peptides (such as, for example, peptides representing soluble extracellular portions of STIF gene product transmembrane receptors), phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, and epitope-binding fragments thereof). Techniques for the determination of effective doses and administration of such compounds are described below.

Further, antisense and ribozyme molecules which inhibit expression of the STIF gene can also be used in accordance with the invention to reduce the level of STIF gene expression, thus effectively reducing the level of STIF gene activity. Still further, triple helix molecules can be utilized in reducing the level of STIF gene activity. Such techniques are described below.

Additionally, techniques for the depletion of specific TH cell subpopulations are discussed below. Such techniques can take advantage of, for example, novel cell surface markers which are specific to the TH cell subpopulation to be depleted, and can include in vivo or in vitro targeted destruction, or, alternatively, selective purification away, of the TH cell subpopulation of interest.

Among the TH cell subpopulation-related sequences identified by the methods described by the present invention is a gene designated herein as the STIF gene, as discussed in the Example presented in Section 6, below. The STIF gene is demonstrated herein to represent a TH2-specific gene in that STIF gene expression is found to be absent TH1 cells as well as all other tissues tested.

The STIF gene and its products can, therefore, be utilized in the treatment of TH2 cell subpopulation-related disorders. For example, a STIF gene product or portions thereof can be utilized, either directly or indirectly, to ameliorate conditions involving inappropriate IgE immune responses, including, but not limited to the symptoms which accompany atopic conditions such as allergy and/or asthma. IgE-type antibodies are produced by stimulated B cells which require, at least in part, IL-4 produced by the TH2 cell subpopulation. Therefore, any treatment, including, for example, the use of a gene STIF product or portion thereof, which reduces the effective concentration of secreted IL-4, e.g., by reducing the number or activity of TH2 cells, can bring about a reduction in the level of circulating IgE, leading, in turn, to the amelioration of the conditions stemming from an inappropriate IgE immune response.

Compounds can be administered which compete with endogenous STIF receptor for the STIF gene product. The resulting reduction in the amount of receptor-bound STIF gene protein will modulate the cellular activity of STIF. Compounds which can be particularly useful for this purpose include, for example, soluble proteins or peptides, or portions and/or analogs thereof, of the gene STIF product, including, for example, soluble fusion proteins such as Ig-tailed fusion proteins. (For a discussion of the production of Ig-tailed fusion proteins see, for example, U.S. Pat. No. 5,116,964.)

The STIF gene product is identified herein as secreted gene product. Further, the STIF gene is shown to exhibit a TH inducible pattern of expression, meaning that STIF gene expression increases in TH2 cell subpopulations in response to stimulation. The STIF gene and its products can, therefore, be utilized in the treatment of a wide range of T cell-related disorders in addition to other STIF based disorders such as proliferative disorders.

Among the compounds which can exhibit the ability to ameliorate STIF related disorder symptoms are antisense, ribozyme, and triple helix molecules. Such molecules can be designed to reduce or inhibit either wild type, or if appropriate, mutant STIF gene activity. Techniques for the production and use of such molecules are well known to those of skill in the art.

Antisense approaches involve the design of oligonucleotides (either DNA or RNA) that are complementary to STIF or pathway gene mRNA. The antisense oligonucleotides will bind to the complementary STIF or pathway gene mRNA transcripts and prevent translation. Absolute complementarily, although preferred, is not required. A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently shown to be effective at inhibiting translation of mRNAs as well. See generally, Wagner, R., 1994, Nature 372:333–335. Thus, oligonucleotides complementary to either the 5'- or 3'-non-translated, non-coding regions of STIF or pathway genes could be used in an antisense approach to inhibit translation of endogenous STIF or pathway gene mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of STIF or pathway gene mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of STIF sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the STIF RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the STIF sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

The antisense molecules should be delivered to cells which express the STIF or pathway gene in vivo. A number of methods have been developed for delivering antisense DNA or RNA to cells; e.g., antisense molecules can be injected directly into the tissue site, or modified antisense molecules, designed to deliver STIF to the desired cells (e.g., antisense linked to peptides or antibodies that specifically bind receptors or antigens expressed on the TH2 cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect STIF cells in the patient will result in the transcription of sufficient amounts of single stranded RNAs that will form complementary base pairs with the endogenous STIF or pathway gene transcripts and thereby prevent translation of the STIF or pathway gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue.

Ribozymes are enzymatic RNA molecules capable of catalyzing the specific cleavage of RNA (For a review see, for example Rossi, J., 1994, Current Biology 4:469–471). The mechanism of ribozyme action involves sequence specific hybridization of the ribozyme molecule to complementary STIF RNA, followed by a endonucleolytic cleavage. The composition of ribozyme molecules must include one or more sequences complementary to the STIF gene mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding STIF gene proteins. Ribozyme molecules designed to catalytically cleave STIF or pathway gene mRNA transcripts can also be used to prevent translation of STIF or pathway gene mRNA and expression of STIF or pathway gene. (See, e.g., PCT International Publication WO90/11364, published Oct. 4, 1990; Sarver et al., 1990, Science 247:1222–1225). While ribozymes that cleave mRNA at site specific recognition sequences can be used to destroy STIF or pathway gene mRNAs, the use of hammerhead ribozymes is preferred. Hammerhead ribozymes cleave mRNAs at locations dictated by flanking regions that form complementary base pairs with the STIF mRNA. The sole requirement is that the STIF mRNA have the following sequence of two bases: 5'-UG-3'. The construction and production of hammerhead ribozymes is well known in the art and is described more fully in Haseloff and Gerlach, 1988, Nature, 334:585–591. Preferably the ribozyme is engineered so that the cleavage recognition site is located near the 5' end of the STIF or pathway gene mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a STIF RNA sequence whereafter cleavage of the STIF RNA takes place. The invention encompasses those Cech-type ribozymes which STIF eight base-pair active site sequences that are present in STIF or pathway gene.

As in the antisense approach, the ribozymes can be composed of modified oligonucleotides (e.g. for improved stability, targeting, etc.) and should be delivered to cells which express the STIF or pathway gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous STIF or pathway gene messages and inhibit translation. Because ribozymes unlike antisense molecules, are catalytic, a lower intracellular concentration is required for efficiency.

In instances wherein the antisense, ribozyme, and/or triple helix molecules described herein are utilized to inhibit mutant gene expression, it is possible that the technique can also efficiently reduce or inhibit the transcription (triple helix) and/or translation (antisense, ribozyme) of mRNA produced by normal STIF gene alleles that the possibility can arise wherein the concentration of normal STIF gene product present can be lower than is necessary for a normal phenotype. In such cases, to ensure that substantially normal levels of STIF gene activity are maintained, therefore, nucleic acid molecules that encode and express STIF gene polypeptides exhibiting normal STIF gene activity can be introduced into cells via gene therapy methods such as those described below, that do not contain sequences susceptible to whatever antisense, ribozyme, or triple helix treatments are being utilized. Alternatively, in instances whereby the STIF gene encodes an extracellular protein, it can be preferable to coadminister normal STIF gene protein in order to maintain the requisite level of STIF gene activity.

Anti-sense RNA and DNA, ribozyme, and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules can be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Endogenous STIF and/or pathway gene expression can also be reduced by inactivating or "knocking out" the STIF and/or pathway gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional STIF and/or pathway gene (or a completely unrelated DNA sequence) flanked by DNA homologous to the endogenous STIF and/or pathway gene (either the coding regions or regulatory regions of the STIF and/or pathway gene) can be used, with or without a selectable marker and/or a negative selectable marker, to transfect cells that express STIF and/or pathway gene in vivo. Insertion of the DNA construct, via targeted homologous recombination, results in inactivation of the STIF and/or pathway gene. Such approaches are particularly suited in the agricultural field where modifications to ES (embryonic stem) cells can be used to generate animal offspring with an inactive STIF and/or pathway gene (e.g., see Thomas & Capecchi 1987 and Thompson 1989, supra). Such techniques can also be utilized to generate T cell subpopulation-related disorder animal models. It should be noted that this approach can be adapted for use in humans provided the recombinant DNA constructs are directly administered or targeted to the required site in vivo using appropriate viral vectors, e.g., herpes virus vectors.

Alternatively, endogenous STIF and/or pathway gene expression can be reduced by targeting deoxyribonucleotide sequences complementary to the regulatory region of the STIF and/or pathway gene (i.e., the STIF and/or pathway gene promoter and/or enhancers) to form triple helical structures that prevent transcription of the STIF or pathway gene in STIF cells in the body. (See generally, Helene, C. 1991, Anticancer Drug Des., 6(6):569–84; Helene, C., et al., 1992, Ann, N.Y. Acad. Sci., 660:27–36; and Maher, L. J., 1992, Bioassays 14(12):807–15). In yet another embodiment of the invention, the activity of STIF and/or pathway gene can be reduced using a "dominant negative" approach. To this end, constructs which encode defective STIF and/or pathway gene products can be used in gene therapy approaches to diminish the activity of the STIF and/or pathway gene product in appropriate STIF cells.

As discussed above, successful treatment of certain STIF related disorders can be brought about by techniques which serve to increase the level of STIF gene expression or to increase the activity of STIF gene product.

For example, compounds such as those identified through assays described, above, in Section 5.3, which exhibit positive modulatory activity can be used in accordance with the invention to ameliorate certain TH cell subpopulation-related disorder symptoms. As discussed in Section 5.3, above, such molecules can include, but are not limited to, peptides representing portions of the STIF gene product, phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, and epitope-binding fragments thereof).

For example, a compound, such as a STIF gene protein, can, at a level sufficient to ameliorate STIF based disorder symptoms, be administered to a patient exhibiting such symptoms. Any of the techniques discussed, below, in Section 5.7, can be utilized for such administration. One of skill in the art will readily know how to determine the concentration of effective, non-toxic doses of the compound, utilizing techniques such as those described, below, in Section 5.7.1.

In instances wherein the compound to be administered is a peptide compound, DNA sequences encoding the peptide compound can be directly administered to a patient exhibiting STIF related disorder symptoms, at a concentration sufficient to produce a level of peptide compound sufficient to ameliorate the disorder symptoms. Any of the techniques discussed, below, in Section 5.7, which achieve intracellular administration of compounds, such as, for example, liposome administration, can be utilized for the administration of such DNA molecules. The DNA molecules can be produced, for example, by well known recombinant techniques.

In the case of peptides, compounds which act extracellularly, the DNA molecules encoding such peptides can be taken up and expressed by any cell type, so long as a sufficient circulating concentration of peptide results for the elicitation of a reduction in the disorder symptoms. In the case of compounds which act intracellularly, the DNA molecules encoding such peptides must be taken up and expressed by the cell subpopulation of interest at a sufficient level to bring about the reduction of disorder symptoms.

For example, any technique which serves to selectively administer DNA molecules to the TH cell subpopulation of interest is, therefore, preferred, for the DNA molecules encoding intracellularly acting peptides. In the case of asthma, for example, techniques for the selective administration of the molecules to TH cell subpopulations residing within lung tissue are preferred.

Further, in instances wherein the TH cell subpopulation-related disorder involves an aberrant STIF gene, patients can be treated by gene replacement therapy. One or more copies of a normal STIF gene or a portion of the gene that directs the production of a normal STIF gene protein with STIF gene function, can be inserted into cells, using vectors which include, but are not limited to adenovirus, adeno-associated virus, and retrovirus vectors, in addition to other particles that introduce DNA into cells, such as liposomes.

Such gene replacement techniques can be accomplished either in vivo or in vitro. As above, for genes encoding extracellular molecules, the cell type expressing the STIF gene is less important than achieving a sufficient circulating concentration of the extracellular molecule for the amelioration of STIF related disorders. In vivo, such techniques can, for example, include appropriate local administration of STIF gene sequences.

Additional methods which may be utilized to increase the overall level of STIF gene expression and/or STIF activity include the introduction of appropriate STIF gene-expressing cells, preferably autologous cells, into a patient at positions and in numbers which are sufficient to ameliorate the symptoms of T cell subpopulation related disorders. Such cells may be either recombinant or non-recombinant. Among the cells which can be administered to increase the overall level of STIF and expression in a patient are normal cells, which express the STIF. The cells can be administered at the anatomical site of expression, or as part of a tissue graft located at a different site in the body. Such cell-based gene therapy techniques are well known to those skilled in the art, see, e.g., Anderson, et al., U.S. Pat. No. 5,399,349; Mulligan & Wilson, U.S. Pat. No. 5,460,959.

In vitro, STIF gene sequences can be introduced into autologous cells. These cells expressing the STIF gene sequence of interest can then be reintroduced, preferably by intravenous administration, into the patient such that there results an amelioration of the symptoms of the disorder.

Alternatively, TH cells belonging to a specific TH cell subpopulation can be administered to a patient such that the overall number of cells belonging to that TH cell subpopulation relative to other TH cell subpopulation cells is increased, which results in an amelioration of a TH cell subpopulation-related disorder.

Described herein are modulatory techniques which, depending on the specific application for which they are utilized, can yield either positive or negative responses leading to the amelioration of immune disorders, including TH cell subpopulation-related disorders. Thus, in appropriate instances, the procedures of this Section can be used in conjunction with the negative modulatory techniques described, above, or, alternatively, in conjunction with the positive modulatory techniques described above.

Antibodies exhibiting modulatory capability can be utilized to ameliorate immune disorders such as TH cell subpopulation-related disorders. Depending on the specific antibody, the modulatory effect can be negative and can, therefore, by utilized as part of the techniques described, above, or can be positive, and can, therefore, be used in conjunction with the techniques described above.

An antibody having negative modulatory capability refers to an antibody which specifically binds to and interferes with the action of a protein. In the case of the secreted STIF gene product, for example, such an antibody would specifically bind to STIF in a manner which does not permit association with the STIF cognate receptor. Such antibodies can be generated using standard techniques described in Section 5.6, above, against full length wild type or mutant proteins, or against peptides corresponding to portions of the proteins. The antibodies include but are not limited to polyclonal, monoclonal, FAb fragments, single chain antibodies, chimeric antibodies, and the like.

An antibody having positive modulatory capability refers to an antibody which specifically binds to a protein and, by binding, serves to, either directly or indirectly, activate the function of the protein which it recognizes. For example, an antibody can bind to the extracellular portion of a transmembrane protein in a manner which causes the transmembrane protein to function as though its endogenous ligand was binding, thus activating, for example, a signal transduction pathway. Antibodies having positive modulatory capability would be those, for example, capable of binding to the natural STIF receptor thereby activating said receptor. Such antibodies can be generated using standard techniques described in Section 5.6, above, against full length wild type or mutant STIF receptor proteins, or against peptides corresponding to portions of the proteins. The antibodies include but are not limited to polyclonal, monoclonal, FAb fragments, single chain antibodies, chimeric antibodies, and the like.

In instances where the protein, such as a STIF gene protein, to which the antibody is directed is intracellular and whole antibodies are used, internalizing antibodies can be preferred. However, lipofectin or liposomes can be used to deliver the antibody or a fragment of the Fab region which binds to the gene product epitope into cells. Where fragments of the antibody are used, the smallest inhibitory fragment which binds to the protein's binding domain is preferred. For example, peptides having an amino acid sequence corresponding to the domain of the variable region of the antibody that binds to the protein can be used. Such peptides can be synthesized chemically or produced via recombinant DNA technology using methods well known in the art (e.g., see Creighton, 1983, supra; and Sambrook et al., 1989, above). Alternatively, single chain antibodies, such as neutralizing antibodies, which bind to intracellular epitopes can also be administered. Such single chain antibodies can be administered, for example, by expressing nucleotide sequences encoding single-chain antibodies within the STIF cell population by utilizing, for example, techniques such as those described in Marasco et al. (Marasco, W. et al., 1993, Proc. Natl. Acad. Sci. USA 90:7889–7893).

In instances where the protein to which the antibody is directed is extracellular, or is a transmembrane protein, any of the administration techniques described, below in Section 5.7 which are appropriate for peptide administration can be utilized to effectively administer the antibodies to their site of action.

5.7. Pharmaceutical Preparations and Methods of Administration

The compounds that are determined to affect STIF gene expression or STIF activity can be administered to a patient at therapeutically effective doses to treat or ameliorate STIF based disorders including proliferative and/or immune disorders. A therapeutically effective dose refers to that amount of the compound sufficient to result in amelioration of symptoms of the various disorders.

5.7.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.7.2. Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5.8. Diagnosis Disorders Associated with Abnormalities in STIF

A variety of methods can be employed for the diagnostic and prognostic evaluation of STIF based disorders, including and for the identification of subjects having a predisposition to such disorders.

Such methods may, for example, utilize reagents such as the STIF nucleotide sequences described in Section 5.1, and STIF antibodies, as described, in Section 5.3. Specifically, such reagents may be used, for example, for: (1) the detection of the presence of STIF gene mutations, or the detection of either over- or under-expression of STIF mRNA relative to the non-disorder state; (2) the detection of either an over- or an under-abundance of STIF gene product relative to the non-disorder state; and (3) the detection of perturbations or abnormalities in the signal transduction pathway mediated by STIF.

The methods described herein may be performed, for example, by utilizing pre-packaged diagnostic kits comprising at least one specific STIF nucleotide sequence or STIF antibody reagent described herein, which may be conveniently used, e.g., in clinical settings, to diagnose patients exhibiting disorder abnormalities.

For the detection of STIF mutations, any nucleated cell can be used as a starting source for genomic nucleic acid. For the detection of STIF gene expression or STIF gene products, any cell type or tissue in which the STIF gene is expressed, may be utilized.

Nucleic acid-based detection techniques are described, below, in Section 5.8.1. Peptide detection techniques are described, below, in Section 5.8.2.

5.8.1. Detection of the STIF Gene and Transcripts

Mutations within the STIF gene can be detected by utilizing a number of techniques. Nucleic acid from any nucleated cell can be used as the starting point for such assay techniques, and may be isolated according to standard nucleic acid preparation procedures which are well known to those of skill in the art.

DNA may be used in hybridization or amplification assays of biological samples to detect abnormalities involving STIF gene structure, including point mutations, insertions, deletions and chromosomal rearrangements. Such assays may include, but are not limited to, Southern analyses, single stranded conformational polymorphism analyses (SSCP), and PCR analyses.

Such diagnostic methods for the detection of STIF gene-specific mutations can involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described in Section 5.1, under conditions favorable for the specific annealing of these reagents to their complementary sequences within the STIF gene. Preferably, the lengths of these nucleic acid reagents are at least 15 to 30 nucleotides. After incubation, all non-annealed nucleic acids are removed from the nucleic acid:STIF molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled STIF nucleic acid reagents is accomplished using standard techniques well-known to those in the art. The STIF gene sequences to which the nucleic acid reagents have annealed can be compared to the annealing pattern expected from a normal STIF gene sequence in order to determine whether an STIF gene mutation is present.

Alternative diagnostic methods for the detection of STIF gene specific nucleic acid molecules, in patient samples or other appropriate cell sources, may involve their amplification, e.g., by PCR (the experimental embodiment set forth in Mullis, K. B., 1987, U.S. Pat. No. 4,683,202), followed by the detection of the amplified molecules using techniques well known to those of skill in the art. The resulting amplified sequences can be compared to those which would be expected if the nucleic acid being amplified contained only normal copies of the STIF gene in order to determine whether an STIF gene mutation exists.

Additionally, well-known genotyping techniques can be performed to identify individuals carrying STIF gene mutations. Such techniques include, for example, the use of restriction fragment length polymorphisms (RFLPs), which involve sequence variations in one of the recognition sites for the specific restriction enzyme used.

Additionally, improved methods for analyzing DNA polymorphisms which can be utilized for the identification of STIF gene mutations have been described which capitalize on the presence of variable numbers of short, tandemly repeated DNA sequences between the restriction enzyme sites. For example, Weber (U.S. Pat. No. 5,075,217, which is incorporated herein by reference in its entirety) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers which are so closely spaced exhibit a high frequency co-inheritance, and are extremely useful in the identification of genetic mutations, such as, for example, mutations within the STIF gene, and the diagnosis of diseases and disorders related to STIF mutations.

Also, Caskey et al. (U.S. Pat. No. 5,364,759, which is incorporated herein by reference in its entirety) describe a DNA profiling assay for detecting short tri and tetra nucleotide repeat sequences. The process includes extracting the DNA of interest, such as the STIF gene, amplifying the extracted DNA, and labelling the repeat sequences to form a genotypic map of the individual's DNA.

The level of STIF gene expression can also be assayed by detecting and measuring STIF transcription. For example, RNA from a cell type or tissue known, or suspected to express the STIF gene may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the STIF gene. Such analyses may reveal both quantitative and qualitative aspects of the expression pattern of the STIF gene, including activation or inactivation of STIF gene expression.

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the STIF nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

fffAdditionally, it is possible to perform such STIF gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (See, for example, Nuovo, G. J., 1992, "PCR In Situ Hybridization: Protocols And Applications", Raven Press, N.Y.).

Alternatively, if a sufficient quantity of the appropriate cells can be obtained, standard Northern analysis can be performed to determine the level of mRNA expression of the STIF gene.

5.8.2. Detection of the STIF Gene Products

Antibodies directed against wild type or mutant STIF gene products or conserved variants or peptide fragments thereof, which are discussed, above, in Section 5.3, may also be used as STIF based disorder diagnostics and prognostics, as described herein. Such diagnostic methods, may be used to detect abnormalities in the level of STIF gene expression, or abnormalities in the structure and/or temporal, tissue, cellular, or subcellular location of the STIF, and may be performed in vivo or in vitro, such as, for example, on biopsy tissue.

For example, antibodies directed to epitopes of the STIF protein can be used in vivo to detect the pattern and level of expression of the STIF in the body. Such antibodies can be labeled, e.g., with a radio-opaque or other appropriate compound and injected into a subject in order to visualize binding to the STIF expressed in the body using methods such as X-rays, CAT-scans, or MRI. Labeled antibody fragments, e.g., the Fab or single chain antibody comprising the smallest portion of the antigen binding region, are preferred for this purpose to promote crossing the blood-brain barrier.

Additionally, any STIF fusion protein or STIF conjugated protein whose presence can be detected, can be administered. For example, STIF fusion or conjugated proteins labeled with a radio-opaque or other appropriate compound can be administered and visualized in vivo, as discussed, above for labeled antibodies.

Alternatively, immunoassays or fusion protein detection assays, as described above, can be utilized on biopsy and autopsy samples in vitro to permit assessment of the expression pattern of the STIF. Such assays are not confined to the use of antibodies that include the use of antibodies directed to epitopes of any of the functional domains of the STIF. The use of each or all of these labeled antibodies will yield useful information regarding translation and intracellular transport of the STIF to the cell surface, and can identify defects in processing.

The tissue or cell type to be analyzed will generally include those which are known, or suspected, to express the STIF gene. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the STIF gene.

For example, antibodies, or fragments of antibodies, such as those described, above, in Section 5.3, useful in the present invention may be used to quantitatively or qualitatively detect the presence of STIF gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred to quantitatively or qualitatively detect cell populations with STIF gene products bound to the surface, i.e., the binding of STIF to its cognate receptor. For example, the expression of STIF on the surface of lympocytes can be used as a marker for detection and/or purification of the TH2 subset of T cells.

The antibodies (or fragments thereof) or natural STIF ligand fusion or conjugated proteins useful in the present invention may, additionally, be employed histologically, as in immunofluorescence, immunoelectron microscopy or non-immuno assays, for in situ detection of STIF gene products or conserved variants or peptide fragments thereof, or for natural STIF receptor binding (in the case of labeled natural STIF fusion protein).

In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of the STIF gene product, or conserved variants or peptide fragments, or natural STIF ligand binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for STIF gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying STIF gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled STIF antibody or natural STIF ligand fusion protein. The solid phase support may then be washed with the buffer a second time to remove unbound antibody or fusion protein. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of STIF antibody or natural STIF fusion protein may be determined according to well known methods. Those skilled in the art will be able to determine operative and optimal assay conditions for each determination by employing routine experimentation.

With respect to antibodies, one of the ways in which the STIF antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect STIF through the use of a radioimmunoassay (RIA) (see, for example, Weintraub, B., Principles of Radioimmunoassays, Seventh Training Course on Radioligand Assay Techniques, The Endocrine Society, March, 1986; which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

6. EXAMPLE

Isolation of an Inducible TH2 Specific Gene Sequence

The differential display technique is a procedure, utilizing the well-known polymerase chain reaction (PCR; the experimental embodiment set forth in Mullis, K. B., 1987, U.S. Pat. No. 4,683,202), which allows for the identification of sequences derived from genes which are differentially expressed. As described below in Section 6.1, such a technique was utilized for the identification of gene sequences which are involved in disorder states, including but not limited to, TH cell subpopulation-related disorder states, and/or which are involved in differentiation, maintenance and/or effector function of TH cell subpopulations.

Briefly, TH cell subpopulations activated with appropriate antigens after which the expression patterns of, e.g. TH1 vs. TH2 and/or activated vs. non-activated cells were analyzed. As described in detail in Section 6.1, activated and non-activated TH1 and TH2 cell lines were analyzed according to such a method.

After stimulation, RNA is isolated and reverse transcribed into single-stranded cDNA, utilizing standard techniques which are well known to those of skill in the art. Next, pairs of PCR primers, as described below, which allow for the quantitative amplification of clones representing a reproducible subset of the RNA transcripts present within any given cell. Utilizing different pairs of primers allows each of the primed mRNA transcripts present in a cell to be amplified. Among such amplified transcripts can be identified those which have been produced from differentially expressed genes.

The pattern of clones resulting from the reverse transcription and amplification of the mRNA of two different cell types is displayed and compared via sequencing gel electrophoresis. Differentially expressed genes are indicated by differences in the two banding patterns. Once identified the band can be purified and used as a probe to screen a library for full length cDNA clones. Such a technique was successfully utilized, as described below, to identify the STIF gene.

The section below describes the identification of a novel gene sequence differentially expressed in a TH2 specific manner.

6.1. Materials and Methods

6.1.1. Stimulation, Cell Culture and Preparation of TH1 and TH2 RNA

To identify gene sequences differentially expressed in TH cell subpopulations, the differential display technique, as described above, was utilized. TH1 and TH2 clonal cell lines were stimulated, and RNA from the cell lines was isolated. Two TH1 (D1.1 and Dorris) and two TH2 (Dax and CDC25) cell lines were utilized. Further, cultures were fed every 2–3 days with fresh IL-2 (Boehringer Mannheim). Cells were cultured according to standard protocols (Coligan, et al., eds., 1995, Current Protocolsin Immunology, John Wiley & Sons, Inc.). Prior to stimulation, cells were starved of both antigen (at least 10 days) and IL-2 (2–3 days), and viable cells were purified with Lymphocyte Separation Medium (Organon Teknika). Cells were separated into two groups. One group was left unstimulated. One group was stimulated for 6 hours by plating on plastic culture dishes which had been coated with anti-mouse CD3 epsilon monoclonal antibody (hybridoma supernatant from the 145-2Cll hybridoma; Parmingen, Inc., San Diego Calif.) at 1.5 ug/ml in PBS for one hour at 37° C.

Total cellular RNA was isolated from the cells of each group (unstimulated or anti-CD3 stimulated) as follows. Specifically, cells were quick frozen on dry ice, homogenized together with a mortar and pestle under liquid nitrogen and total cellular RNA was extracted from cells with RNAzol(TM) (TEL-TEST, Inc., Friendswood Tex.) according to the manufacturer's instructions. Briefly, the cells were solubilized in an appropriate amount of RNAzol(TM) and RNA was extracted by the addition of 1/10 v/v chloroform to the solubilized sample followed by vigorous shaking for approximately 15 seconds. The mixture was then centrifuged for 15 minutes at 12,000 g and the aqueous phase was removed to a fresh tube. RNA was precipitated with isopropanol. The resultant RNA pellet was dissolved in water and re-extracted with an equal volume of chloroform to remove any remaining phenol. The extracted volume was precipitated with 2 volumes of ethanol in the presence of 150 mM sodium acetate. The precipitated RNA was dissolved in water and the concentration determined spectroscopically (A260). Residual DNA was removed by digesting for 30 min at 37° C. with RNAse free DNAse I (Boehringer Mannheim). After extraction with phenol/chloroform and ethanol precipitation, the RNA was dissolved in DEPC (diethyl pyrocarbonate)-treated water.

RNA populations from the two different stimulated and unstimulated TH1 and TH2 cell lines were compared using the Delta RNA Fingerprinting Kit (Clontech #PT1173-1), according to the manufacturer's protocol.

6.1.2. Identification of a TH2 Specific Gene Sequence

The RNA isolated for TH1 and TH2 cells, as described, above, was quantitatively amplified and the cells, gene expression patterns were analyzed as described herein. The analysis yielded an approximately 297 bp differentially expressed cDNA gene sequence which, interestingly, was expressed exclusively in the two TH2 clones examined, but was absent in non-stimulated TH2 clones and in all the TH1 clones examined.

Specifically, cDNA synthesis was performed using DNA free RNA from 2 independent TH1 clones and 2 independent TH2 clones. For each sample, cDNA synthesis was performed using 2 ug of total RNA and 1 ul of oligo dT primer (1 uM), as described in the manufacturer's protocol. cDNA samples were stored at −20° C., and used for PCR amplification using various combinations of the following 26 bp 5' (P primers) and 30 bp 3' (T primers):

P: 5'-ATTAACCCTCACTAAAGATCTGACTG-3' (forward primer) (SEQ ID NO:7)

and

T: 5'-CATTATGCTGAGTGATATCTTTTTTTTCC-3' (reverse primer). (SEQ ID NO:8)

PCR amplification was performed according to the provided protocol, using the CLONTECH Advantage cDNA PCR Core Kit (K1905-1). Three low stringency PCR cycles (annealing temp. 40° C.) were followed by 22–25 high stringency PCR cycles (annealing temp. 60° C.), and PCR products were separated by denaturing PAGE using 5% polyacrylamide/8M urea gels, and PCR products were visualized by autoradiography. Differentially expressed bands were excised from dried gels and re-amplified using the original primers. Re-amplified products were cloned into pCR 2.1, using the TA Cloning Kit (Invitrogen), and individual isolates were sequenced.

6.1.3. Cloning and Characterization of STIF, A Novel TH2-Specific Gene

The STIF gene was obtained by screening of a TH2-specific cDNA library with the 297bp cDNA fragment described above. A TH2-specific cDNA library was screened in an attempt to obtain the full-length sequence corresponding to the 297 bp sequence identified in Section 6.2, above. A TH2-specific cDNA library was generated using polyA+ RNA isolated from the TH2 cell line D1OG4 (anti-CD3 stimulated), using the Fast Track 2.0 Kit (Invitrogen). cDNA was generated using oligo dT primers and cloned into lambda ZIPLOX phage arms (GIBCOBRL 15394-018), Using the Sal I and Not I cloning sites. The TH-2 specific phage library was screened using a labeled probe generated from the re-amplified 297 bp fragment obtained by the differential display method to described above. Briefly, plaques were screened with the probe overnight at 65° C. in Church's buffer (7% SDS, 250 mM NaHP04, 3 $\mu$m EDTA, 1% BSA). The next day, filters were washed in 2× SSC/1% SDS 30 minutes at 50° C. Positive plaques-were rescreened under the same conditions.

6.1.4. Expression of STIF Genes

Northern blot analysis was carried out to determine the size of the STIF transcript and the tissue distribution of STIF expression. As described below, the expression analysis confirmed the TH2-specific STIF gene expression pattern and, further, revealed that the gene produces a transcript of approximately 1.1 kb.

For northern analysis of murine tissues, total cellular RNA from various murine tissues (spleen, thymus, lymph node, muscle, heart, liver, kidney, brain, uterus and testes) was isolated using the RNA purification techniques as described above. Cell lines tested included the following: WEHI-3B myelomonocyte, Pu5-1.8 myelomonocyte, P388D1 monocyte-macrophage, IC-21 macrophage, AKR.G2 thyoma, BaF3 pro B-cell, EL-4 lymphoma, NFS-1.0 C-1 B-cell lymphoma, SOT embryonic fibroblast, EOMA endothelial and BMS-12 bone marrow. Stimulated and unstimulated TH1 clones D1.1, Dorris and AE7, and TH2 clones D1O.G4, DAX and CDC25 were also tested. The TH-1 and TH-2 clones were cultured and stimulated as described above in Section 6.1.1. RNA samples were electrophoresed in a denaturing agarose gel containing 1–1.5% agarose (SeaKem LE, FMC BioProducts, Rockland, Me.) containing 3% formaldehyde. For northern analysis of hematopoietic cell lines, a total of approximately 20 $\mu$g of total RNA was loaded per lane, for all other cell lines approximately 15 $\mu$g of total RNA was loaded per lane. Samples containing the indicated amounts of total RNA were mixed with denaturing loading solution (72% deionized formamide and bromophenol blue) and heated to 70° C. for 5 minutes. Samples were placed on ice and immediately loaded onto gels. Gels were run in 1× MOPS buffer (100 mM MOPS, 25 mM sodium acetate, 5 mM EDTA). After electrophoresis, the gels were stained with ethidium bromide and visualized with ultraviolet light.

After completion of electrophoresis, gels were soaked in 50 mM sodium hydroxide with gentle agitation for approximately 30 minutes to lightly cleave RNA. Gels were rinsed twice in water and then neutralized by soaking in 0.1M Tris-HCl (pH 7.5) for approximately 30 minutes. Gels were briefly equilibrated with 20× SSC (3M sodium chloride, 0.3M sodium citrate) and then transferred to nylon membranes such as Hybond N, (Amersham, Inc., Arlington Heights, Ill.) or ZetaProbe (Bio-Rad, Inc., Hercules, Calif.) overnight in 20× SSC. Membranes containing transferred RNA were baked at 800° C. for hours to immobilize the RNA.

The 297 bp STIF probe was prepared as follows.

Briefly, 50 ng of purified DNA fragment was used to generate the probe. The fragment was added to a 20 µl random hexanucleotide labeling reaction (Boehringer Mannhein, Inc., Indianapolis, Ind.) containing random hexamers and a mix of the nucleotides dCTP, dGTP, and dTTP (at a final concentration of 25 µM each). The reaction mix was heat-denatured at 100° C. for 10 minutes and then chilled on ice. 5 µl of alpha $^{32}$P-dATP (5 µCi Amersham, Inc., Arlington Heights, Ill.) and Klenow DNA polymerase (2 units; Boehringer Mannheim, Inc., Indianapolis, Ind.) were added. Reactions were incubated at 37° C. for 30 minutes. Following incubation, 30 µl water was added to the labeling reaction and unincorporated nucleotides were removed by passing the reactions through a BioSpin-67M chromatography column (Bio-Rad, Inc., Hercules, Calif.). Specific incorporation was determined using a scintillation counter. 1–5 X106 cpm were used per ml hybridization mixture.

Nylon membranes containing immobilized RNA were prehybridized according to manufacturer's instructions. Radiolabelled probes were heat denatured at 100° C. in 50% deionized formamide for 10 minutes and then added to the hybridization mixture Rapid-hyb buffer (Amersham Life Science, Cat #RPN1635).

Hybridizations were carried out at 65° C. overnight. Nylon membranes were then bathed for 2 minutes in a wash solution of 0.2× SSC and 0.1% SDS at room temperature to remove most of the remaining hybridization solution. The membranes were then bathed twice in fresh 42° C. preheated wash solution for 20 minutes. Filters were covered in plastic wrap and exposed to autoradiographic film to visualize results.

6.1.5. Chromosomal Mapping of the STIF Gene

To determine the chromosomal map position of the STIF gene the technique of Single Stranded Conformational Polymorphism (SSCP) gel electrophoresis was used. More specifically, the genetic segregation of the *Mus spretus* allele of STIF was followed in 188 backcross progeny of cross (C57B1/6J×*Mus spretus*) F1 females×C57B1/6J males. PCR primers were designed from the 3' UTR of STIF cDNA. The following STIF derived PCR primers were used for amplification of mouse genomic DNA:

```
5'-GGATGCTCCGACTGACCC-3'
    (forward primer)                    (SEQ ID NO:9)

5'-CTGAGCAACCATCCACTGCC-3'
    (reverse primers).                   (SEQ ID NO:10)
```

The PCR reaction mixture contained 6 µl template DNA (10 ng/µl), 1.4 µl 10× Perkin Elmer (Norwalk, Conn.) PCR buffer, 1.12 µl dNTPs (2.5 mill), 1.05 µl Forward primer (6 µM), 1.05 µl Reverse primer (6uM), 0.38 µl H$_2$O and 3 µl Amplitaq Hotstart polymerase (Perkin Elmer; 0.5 U/µl).

The amplification profile was as follows: 94° C., 2 minutes, at which point the Amplitaq was added; then 30 cycles of 94° C., 40 seconds; 55° C., 50 seconds; and 72° C., 30 seconds. Samples were run on both (a) nondenaturing 8% acrylamide gels run at 45 W, room temperature, for 3 hours and (b) nondenaturing 10% acrylamide SSCP (single stranded conformational polymorphism) gels run at 20 W, 4-C, for 2.5 hours. Both types of gels were stained with SYBR Green I and scanned on an MD fluorimager, and gave interpretable results. The primers amplified a 194 bp fragment from C57B1/6J *Mus spretus* genomic DNA, consistent with the base pair length between the two primers in the STIF cDNA.

6.1.6. STIF is a Secreted Protein

The coding region for STIF-1 was fused to an antigenic tag and cloned into the eukaryotic expression vector pcDNA3 for functional analysis of the STIF-1 protein. The coding region was amplified, using the polymerase chain reaction (PCR), from the original cDNA clone. PCR primers were designed as follows: The 5' primer was designed to begin at the first ATG for the longest open reading frame detected (A$_{73}$). Additionally, a SalI cloning site was inserted at the extreme 5' end (5'-CGGGATCCGTCGACATGCT-GACTGAGCCTGCCCAAC-3'(SEQ ID NO:11)).

The Flag antigenic tag (IBI, New Haven, Conn.) was fused to the C-terminus of the predicted coding region (ending at position C$_{732}$), and XbaI cloning site was inserted at the extreme 3' end (5'-GCTCTAGACTCGAGTCACT-TGTCATCGTCGTCCTTGTAGTCGAGATGGTAGAAT-TTCTGCATCC-3' (SEQ ID NO:12)).

An equivalent construct was made containing the IL-10 coding region. PCR primers were designed as follows:

```
5' primer: 5'-CGGGATCCGTCGACCATTTAGAGACTTGCTCTTGCACT-3'  (SEQ ID NO: 13)

3' primer: 5'-GCTCTAGACTCGAGTCACTTGTCATCGTCGTCCTTGTAG-
               TCGCTTTTCATTTTGATCATCATGTATG-3'  (SEQ ID NO: 14).
```

The IL-10 coding region was amplified from cDNA derived from two Th2 cell lines (D10.G4 and Dax described above).

The above cDNA inserts were digested with SalI and XbaI, and cloned into the XhoI and XbaI sites of pcDNA3.

The STIF coding region was cloned into each of the above identified plasmids. 293 cells were then transfected with each of the above identified plasmid constructs utilizing Lipofectamine (Gibco BRL). Four days following transfection, cell supernatants were collected and immunoprecipitated with anti-flag antibody according to manufacturers instructions. Ten microliters of immunoprecipitated protein was mixed with running buffer and loaded on a 12% SDS-PAGE gel (BioRad). The gel was electrophoresed and transferred to a nylon membrane by standard techniques. Western blotting was done and the filter was probed with an anti-flag antibody followed by a anti-mouse peroxidase conjugated antibody. The Western Blot was visualized using the ECL system (Amersham).

6.1.7. Cloning and Characterization of Human STIF

A cDNA library was constructed from bronchial epithelial cell RNA by first and second strand synthesis. RNA was isolated according to the method of Chirgwin et al. (1979, Biochemistry 18:5294) using guanidine isothiocyonide/CsCl. Poly A+ RNA was isolated using an oligotex-dT kit (Qiagen, Chatsworth). The cDNA was fractionated as described in the protocol from the Gibco BRL kit "Super-script" Plasmid System for cDNA synthesis and Plasmid Cloning". cDNA representing the largest fractions was ligated into lambda ZlPLOX (Gibco BRL) and packaged (Stratagene Gigapack II Gold) and amplified as directed by manufacturer (Stratagene, La Jolla, Calif.).

To isolate a cDNA clone a 400 bp probe was generated by PCR using the following primer pairs:

```
5'TTACCCTGCTTCTCTGG3'      (SEQ ID NO:15)
5'TCCATCAGAGACAGTCA3'      (SEQ ID NO:16)
``` and labeled using the Random Primer Kit from Stratagene.

The cDNA library generated as described above was probed by hybridization at 60° C. overnight using Amersham Rapid Hybridization Buffer (Cat. No. RPN1639) according to the manufacturers protocol. A final wash was performed in nylon wash (14% SDS, 130 mM $Na_2HPO_4$, 14 mM NaEDTA, 0.2% Triton X-100) at 60° C. Positive clones were identified by sequencing using standard automated fluorescent dideoxynucleotide sequencing using dye-primer chemistry (Applied Biosystems, Inc., Foster City, Calif.) on Applied Biosystems 373 and 377 sequanators (Applied Biosystems).

6.2 Results

6.2.1. Characterization of the STIF TH2 Differentially Expressed Gene

The largest murine positive clone obtained was 1138 bp, and contained one complete open reading frame, which codes for a 220 amino acid protein having a predicted molecular weight of 25.2 kD. The gene/protein is now referred to as STIF. The murine STIF nucleotide and amino acid sequences are depicted in FIG. 1.

Comparison of the murine STIF sequence to known genes (Altschul, S. F. et al., 1990, J. Mol. Biol. 215:403–410) indicates that STIF is approximately 66.5% identical to human MDA-7 and 34% over 53 amino acids to murine IL-10.

In addition, two human STIF cDNA clones were obtained. As shown in FIGS. 2A–C, one clone contained one complete open reading frame, which codes for a 179 amino acid protein. The second human STIF nucleotide and amino aced sequences are depicted in FIG. 3. The STIF clone depicted in FIG. 3, shares homology with the human MDA-7 gene with an additional SER residue inserted at position number 15.

6.2.2 Northern Blot Analysis of STIF Expression

Northern Blot analyses verify that the STIF gene is highly unregulated in stimulated TH2 cells. First, northern blot analysis of 3 individual TH1 clones and 3 individual TH2 clones revealed an approximately 1.1 kb RNA which is highly unregulated in stimulated TH2 clones, but is absent from all other samples tested. Consistent with the cell clone data, STIF message appears to be absent from all of other murine tissues analyzed (i.e., spleen, thymus, lymph node, muscle, heart, liver, kidney, brain, uterus and testes), although the STIF probe clearly hybridized with itself. Third, northern blot analysis was also performed with a panel of murine hematopoietic cell lines. RNA was obtained from various cell lines which had either been left unstimulated or had been stimulated with appropriate antigen (i.e., either PMA or LPS, as described, above, in Section 6.2). STIF RNA was not detected in any of the cell lines tested (Pu51.8, STO,EOMA and BMS12).

6.2.3. STIF is a Secreted Polypeptide

Cells transfected with flagged IL-10 showed two bands at 20 and 17 kd. IL-10 is a known dimer. Cells transfected with the STIF flag construct gave a band at roughly between 20–25 kd indicating that the STIF protein is a secreted polypeptide. The vector control showed no bands.

6.2.4. Chromosomal Mapping of the Murine STIFF Gene

The segregation pattern of the *Mus spretus* allele was compared to the segregation pattern of 255 other genetic loci that have been mapped in this backcross panel. By minimizing the number of multiple crossovers between STIF and other markers it was determined that STIF maps to murine chromosome 1, 4.6 CM distal of DIMIT12 and 5.03 cM proximal of DIMIT 17.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated nucleic acid molecule consisting of a nucleotide sequence which encodes the amino acid sequence of SEQ ID NO:4.

2. An isolated nucleic acid molecule comprising fee nucleotide sequence of SEQ ID NO:3.

3. An isolated nucleic acid molecule consisting of a nucleotide sequence encoding the amino acid sequence encoded by the nucleic acid insert of the clone contained in ATCC Accession No 98427.

4. An isolated nucleic acid molecule comprising a nucleotide sequence which encodes the amino acid sequence of SEQ ID NO:6.

5. The isolated nucleic acid molecule of claim 4, wherein the nucleic acid molecule comprises the nucleotide sequence of SEQ ID NO:5.

6. An isolated nucleic acid molecule comprising a nucleotide sequence which differentially hybridizes to the complement of a nucleotide sequence which comprises nucleotides 1 to 17 of the nucleotide sequence SEQ ID NO:3 under hybridization conditions comprising in 0.5M NaHP04, 7% SDS, 1 nM EDTA, and washing in 6× SSC/ 0.5% sodium pyrophosphate at 37° C.

7. An isolated nucleic acid molecule encoding a peptide comprising amino acid residues 1 to 28 of the polypeptide sequence of SEQ ID NO:6.

8. The isolated nucleic acid molecule of claim 7, wherein the nucleic acid molecule comprises nucleotides 1 to 84 of the nucleotide sequence of SEQ ID NO:5.

9. An isolated nucleic acid molecule comprising a nucleotide sequence which encodes an epitope of the polypeptide of SEQ ID NO:6 wherein the epitope contains amino acid residue 15 of said polypeptide sequence.

10. A vector containing the nucleotide sequence of any one of claims 1–5.

11. A vector containing the nucleotide sequence of any one of claims 6–9.

12. An expression vector containing the nucleotide sequence of any one of claims 1–5 in operative association with a nucleotide regulatory sequence that controls expression of the nucleotide sequence in a host cell.

13. An expression vector containing the nucleotide sequence of any one of claims 6–9 in operative association with a nucleotide regulatory sequence that controls expression of the nucleotide sequence in a host cell.

14. A host cell genetically engineered to contain the nucleotide sequence of any one of claims 1–5.

15. A host cell genetically engineered to contain the nucleotide sequence of any one of claims 6–9.

16. A host cell genetically engineered to contain the nucleotide sequence of any one of claims 1–5 in operative association with a nucleotide regulatory sequence that controls expression of the nucleotide sequence in the host cell.

17. A host cell genetically engineered to contain the nucleotide sequence of any one of claims 6–9 in operative association with a nucleotide regulatory sequence that controls expression of the nucleotide sequence in the host cell.

\* \* \* \* \*

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 1018 base pairs
      (B) TYPE: nucleic acid
      (C) STRANDEDNESS: single
      (D) TOPOLOGY: linear (ii) MOLECULE TYPE: DNA (ix) FEATURE:
 (A) NAME/KEY: Coding Sequence
 (B) LOCATION: 73...732
 (D) OTHER INFORMATION:

(xi) SEQUENCE DESCRIPTION: SEQ ID NO:1:

```
CGACCCACGC GTCCGATCAT TTCCACAGCT GAGAAGGAGC TTCCCACCCA GCAGAAGATC      60

CTCTACCAAT GA ATG CTG ACT GAG CCT GCC CAA CTT TTT GTG CAC AAG AAG     111
              Met Leu Thr Glu Pro Ala Gln Leu Phe Val His Lys Lys
                1           5                  10

AAC CAG CCA CCT TCA CAC AGC AGC CTC CGG CTT CAC TTT AGG ACC CTA       159
Asn Gln Pro Pro Ser His Ser Ser Leu Arg Leu His Phe Arg Thr Leu
 15              20                  25

GCA GGA GCA CTG GCC CTT TCT TCA ACA CAG ATG AGT TGG GGA CTA CAG       207
Ala Gly Ala Leu Ala Leu Ser Ser Thr Gln Met Ser Trp Gly Leu Gln
 30              35                  40                  45

ATT CTC CCC TGC CTG AGC CTA ATC CTT CTT CTT TGG AAC CAA GTG CCA       255
Ile Leu Pro Cys Leu Ser Leu Ile Leu Leu Leu Trp Asn Gln Val Pro
                 50                  55                  60

GGG CTT GAG GGT CAA GAG TTC CGA TTT GGG TCT TGC CAA GTG ACA GGG       303
Gly Leu Glu Gly Gln Glu Phe Arg Phe Gly Ser Cys Gln Val Thr Gly
             65                  70                  75

GTG GTT CTC CCA GAA CTG TGG GAG GCC TTC TGG ACT GTG AAG AAC ACT       351
Val Val Leu Pro Glu Leu Trp Glu Ala Phe Trp Thr Val Lys Asn Thr
         80                  85                  90

GTG CAA ACT CAG GAT GAC ATC ACA AGC ATC CGG CTG TTG AAG CCG CAG       399
Val Gln Thr Gln Asp Asp Ile Thr Ser Ile Arg Leu Leu Lys Pro Gln
     95                 100                 105

GTT CTG CGG AAT GTC TCG GGT GCT GAG AGC TGT TAC CTT GCC CAC AGC       447
Val Leu Arg Asn Val Ser Gly Ala Glu Ser Cys Tyr Leu Ala His Ser
110                 115                 120                 125

CTG CTG AAG TTC TAC TTG AAC ACT GTT TTC AAG AAC TAC CAC AGC AAA       495
Leu Leu Lys Phe Tyr Leu Asn Thr Val Phe Lys Asn Tyr His Ser Lys
                130                 135                 140

ATA GCC AAA TTC AAG GTC TTG AGG TCA TTC TCC ACT CTG GCC AAC AAC       543
Ile Ala Lys Phe Lys Val Leu Arg Ser Phe Ser Thr Leu Ala Asn Asn
            145                 150                 155

TTC ATA GTC ATC ATG TCA CAA CTA CAG CCC AGT AAG GAC AAT TCC ATG       591
Phe Ile Val Ile Met Ser Gln Leu Gln Pro Ser Lys Asp Asn Ser Met
        160                 165                 170

CTT CCC ATT AGT GAG AGT GCA CAC CAG CGG TTT TTG CTG TTC CGC AGA       639
Leu Pro Ile Ser Glu Ser Ala His Gln Arg Phe Leu Leu Phe Arg Arg
    175                 180                 185

GCA TTC AAA CAG TTG GAT ACA GAA GTC GCT TTG GTG AAA GCC TTT GGG       687
Ala Phe Lys Gln Leu Asp Thr Glu Val Ala Leu Val Lys Ala Phe Gly
190                 195                 200                 205

GAA GTG GAC ATT CTC CTG ACC TGG ATG CAG AAA TTC TAC CAT CTC TGACT    737
Glu Val Asp Ile Leu Leu Thr Trp Met Gln Lys Phe Tyr His Leu
                210                 215                 220

GCTGATTGGA TAACTTCCTC CTTTGCTCTC CATGCCATTT CAAGGCATTG TGTACATCCC    797

TGCTGTCCTC AAGGCACTTC AGACCCTTGG CCATGGACCC CGTTGTTGGC TCAGGCTTTT    857

CCTCAGACCT CACTCTTCAG TCCAAATGAC AGCCATAGAT GGCACCTTTG GATGCTCCGA    917

CTGACCCACA AAGTAGATTT GCATATTTAT TACAGCCCTA TTAAATTATT GTCACCTTCC    977

CTGGAAACCG TATTTATTTG TGAGACCAGA AGTTCCATGA A                       1018
```

(2) INFORMATION FOR SEQ ID NO:2:

(i) SEQUENCE CHARACTERISTICS:
        (A) LENGTH: 220 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:2:

```
Met Leu Thr Glu Pro Ala Gln Leu Phe Val His Lys Lys Asn Gln Pro
 1               5                  10                  15

Pro Ser His Ser Ser Leu Arg Leu His Phe Arg Thr Leu Ala Gly Ala
            20                  25                  30

Leu Ala Leu Ser Ser Thr Gln Met Ser Trp Gly Leu Gln Ile Leu Pro
        35                  40                  45

Cys Leu Ser Leu Ile Leu Leu Leu Trp Asn Gln Val Pro Gly Leu Glu
 50                  55                  60

Gly Gln Glu Phe Arg Phe Gly Ser Cys Gln Val Thr Gly Val Val Leu
 65                  70                  75                  80

Pro Glu Leu Trp Glu Ala Phe Trp Thr Val Lys Asn Thr Val Gln Thr
                85                  90                  95

Gln Asp Asp Ile Thr Ser Ile Arg Leu Leu Lys Pro Gln Val Leu Arg
            100                 105                 110

Asn Val Ser Gly Ala Glu Ser Cys Tyr Leu Ala His Ser Leu Leu Lys
        115                 120                 125

Phe Tyr Leu Asn Thr Val Phe Lys Asn Tyr His Ser Lys Ile Ala Lys
    130                 135                 140

Phe Lys Val Leu Arg Ser Phe Ser Thr Leu Ala Asn Asn Phe Ile Val
145                 150                 155                 160

Ile Met Ser Gln Leu Gln Pro Ser Lys Asp Asn Ser Met Leu Pro Ile
                165                 170                 175

Ser Glu Ser Ala His Gln Arg Phe Leu Leu Phe Arg Arg Ala Phe Lys
            180                 185                 190

Gln Leu Asp Thr Glu Val Ala Leu Val Lys Ala Phe Gly Glu Val Asp
        195                 200                 205

Ile Leu Leu Thr Trp Met Gln Lys Phe Tyr His Leu
    210                 215                 220
```

(2) INFORMATION FOR SEQ ID NO:3:

(i) SEQUENCE CHARACTERISTICS:
        (A) LENGTH: 1568 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 209...745
        (D) OTHER INFORMATION:

(xi) SEQUENCE DESCRIPTION: SEQ ID NO:3:

```
GTCGACCCAC GCGTCCGCTG AAATGACTTC CACGGCTGGG ACGGGAACCT TCCACCCACA    60

GCTATGCCTC TGATTGGTGA ATGGTGAAGG TGCCTGTCTA ACTTTTCTGT AAAAAGAACC   120

AGCTGCCTCC AGGCAGCCAG CCCTCAAGCA TCACTTACAG GACCAGAGCA GACCCTTCTG   180
```

```
CCCTCCTTTG CTGGCGACAG CCTCTCAA ATG CAG ATG GTT GTG CTC CCT TGC         232
                               Met Gln Met Val Val Leu Pro Cys
                                 1               5

CTG GGT TTT ACC CTG CTT CTC TGG AGC CAG GTA TCA GGG GCC CAG GGC        280
Leu Gly Phe Thr Leu Leu Leu Trp Ser Gln Val Ser Gly Ala Gln Gly
     10              15                  20

CAA GAA TTC CAC TTT GGG CCC TGC CAA GTG AAG GGG GTT GTT CCC CAG        328
Gln Glu Phe His Phe Gly Pro Cys Gln Val Lys Gly Val Val Pro Gln
 25              30                  35                  40

AAA CTG TGG GAA GCC TTC TGG GCT GTG AAA GAC ACT ATG CAA GCT CAG        376
Lys Leu Trp Glu Ala Phe Trp Ala Val Lys Asp Thr Met Gln Ala Gln
             45                  50                  55

GAT AAC ATC ACG AGT GCC CGG CTG CTG CAG CAG GAG GTT CTG CAG AAC        424
Asp Asn Ile Thr Ser Ala Arg Leu Leu Gln Gln Glu Val Leu Gln Asn
                 60                  65                  70

GTC TCG GAT GCT GAG AGC TGT TAC CTT GTC CAC ACC CTG CTG GAG TTC        472
Val Ser Asp Ala Glu Ser Cys Tyr Leu Val His Thr Leu Leu Glu Phe
             75                  80                  85

TAC TTG AAA ACT GTT TTC AAA AAC TAC CAC AAT AGA ACA GTT GAA GTC        520
Tyr Leu Lys Thr Val Phe Lys Asn Tyr His Asn Arg Thr Val Glu Val
         90                  95                 100

AGG ACT CTG AAG TCA TTC TCT ACT CTG GCC AAC AAC TTT GTT CTC ATC        568
Arg Thr Leu Lys Ser Phe Ser Thr Leu Ala Asn Asn Phe Val Leu Ile
105             110                 115                 120

GTG TCA CAA CTG CAA CCC AGT CAA GAA AAT GAG ATG TTT TCC ATC AGA        616
Val Ser Gln Leu Gln Pro Ser Gln Glu Asn Glu Met Phe Ser Ile Arg
                125                 130                 135

GAC AGT GCA CAC AGG CGG TTT CTG CTA TTC CGG AGA GCA TTC AAA CAG        664
Asp Ser Ala His Arg Arg Phe Leu Leu Phe Arg Arg Ala Phe Lys Gln
                140                 145                 150

TTG GAC GTA GAA GCA GCT CTG ACC AAA GCC CTT GGG GAA GTG GAC ATT        712
Leu Asp Val Glu Ala Ala Leu Thr Lys Ala Leu Gly Glu Val Asp Ile
            155                 160                 165

CTT CTG ACC TGG ATG CAG AAA TTC TAC AAG CTC TGAATGTCTA GACCAGGACC      765
Leu Leu Thr Trp Met Gln Lys Phe Tyr Lys Leu
        170                 175

TCCCTCCCCC TGGCACTGGT TTGTTCCCTG TGTCATTTCA AACAGTCTCC CTTCCTATGC      825

TGTTCACTGG ACACTTCACG CCCTTGGCCA TGGGTCCCAT TCTTGGCCCA GGATTATTGT      885

CAAAGAAGTC ATTCTTTAAG CAGCGCCAGT GACAGTCAGG GAAGGTGCCT CTGGATGCTG      945

TGAAGAGTCT ACAGAAGAGA TTCTTGTATT TATTACAACT CTATTTAATT AATGTCAGTA     1005

TTTCAACTGA AGTTCTATTT ATTTGTGAGA CTGTAAGTTA CATGAAGGCA GCAGAATATT     1065

GTGCCCCATG CTTCTTTACC CCTCACAATC CTTGCCACAG TGTGGGCAG TGGATGGGTG      1125

CTTAGTAAGT ACTTAATAAA CTGTGGTGCT TTTTTTGGCC TGTCTTTGGA TTGTTAAAAA     1185

ACAGAGAGGG ATGCTTGGAT GTAAAACTGA ACTTCAGAGC ATGAAAATCA CACTGTCTTC     1245

TGATATCTGC AGGGACAGAG CATTGGGGTG GGGGTAAGGT GCATCTGTTT GAAAAGTAAA     1305

CGATAAAATG TGGATTAAAG TGCCCAGCAC AAAGCAGATC TCAATAAAC ATTTCATTTC      1365

CCACCCACAC TCGCCAGCTC ACCCCATCAT CCCTTTCCCT TGGTGCCCTC CTTTTTTTTT     1425

TATCCTAGTC ATTCTTCCCT AATCTTCCAC TTGAGTGTCA AGCTGACCTT GCTGATGGTG     1485

ACATTGCACC TGGATGTACT ATCCAATCTG TGATGACATT CCCTGCTAAT AAAAGACAAC     1545

ATAACTCAAA AAAAAAAAAA AAA                                            1568
```

(2) INFORMATION FOR SEQ ID NO:4:

(i) SEQUENCE CHARACTERISTICS:
        (A) LENGTH: 179 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:4:

```
Met Gln Met Val Val Leu Pro Cys Leu Gly Phe Thr Leu Leu Leu Trp
 1               5                  10                  15

Ser Gln Val Ser Gly Ala Gln Gly Gln Glu Phe His Phe Gly Pro Cys
            20                  25                  30

Gln Val Lys Gly Val Val Pro Gln Lys Leu Trp Glu Ala Phe Trp Ala
        35                  40                  45

Val Lys Asp Thr Met Gln Ala Gln Asp Asn Ile Thr Ser Ala Arg Leu
50                  55                  60

Leu Gln Gln Glu Val Leu Gln Asn Val Ser Asp Ala Glu Ser Cys Tyr
65                  70                  75                  80

Leu Val His Thr Leu Leu Glu Phe Tyr Leu Lys Thr Val Phe Lys Asn
                85                  90                  95

Tyr His Asn Arg Thr Val Glu Val Arg Thr Leu Lys Ser Phe Ser Thr
            100                 105                 110

Leu Ala Asn Asn Phe Val Leu Ile Val Ser Gln Leu Gln Pro Ser Gln
        115                 120                 125

Glu Asn Glu Met Phe Ser Ile Arg Asp Ser Ala His Arg Arg Phe Leu
    130                 135                 140

Leu Phe Arg Arg Ala Phe Lys Gln Leu Asp Val Glu Ala Ala Leu Thr
145                 150                 155                 160

Lys Ala Leu Gly Glu Val Asp Ile Leu Leu Thr Trp Met Gln Lys Phe
                165                 170                 175

Tyr Lys Leu
```

(2) INFORMATION FOR SEQ ID NO:5:

(i) SEQUENCE CHARACTERISTICS:
        (A) LENGTH: 624 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 1...621
        (D) OTHER INFORMATION:

(xi) SEQUENCE DESCRIPTION: SEQ ID NO:5:

```
ATG AAT TTT CAA CAG AGG CTG CAA AGC CTG TGG ACT TTA GCC AGC AGA      48
Met Asn Phe Gln Gln Arg Leu Gln Ser Leu Trp Thr Leu Ala Ser Arg
 1               5                  10                  15

CCC TTC TGC CCT CCT TTG CTG GCG ACA GCC TCT CAA ATG CAG ATG GTT      96
Pro Phe Cys Pro Pro Leu Leu Ala Thr Ala Ser Gln Met Gln Met Val
            20                  25                  30

GTG CTC CCT TGC CTG GGT TTT ACC CTG CTT CTC TGG AGC CAG GTA TCA     144
Val Leu Pro Cys Leu Gly Phe Thr Leu Leu Leu Trp Ser Gln Val Ser
        35                  40                  45
```

```
GGG GCC CAG GGC CAA GAA TTC CAC TTT GGG CCC TGC CAA GTG AAG GGG        192
Gly Ala Gln Gly Gln Glu Phe His Phe Gly Pro Cys Gln Val Lys Gly
             50                  55                  60

GTT GTT CCC CAG AAA CTG TGG GAA GCC TTC TGG GCT GTG AAA GAC ACT        240
Val Val Pro Gln Lys Leu Trp Glu Ala Phe Trp Ala Val Lys Asp Thr
 65                  70                  75                  80

ATG CAA GCT CAG GAT AAC ATC ACG AGT GCC CGG CTG CTG CAG CAG GAG        288
Met Gln Ala Gln Asp Asn Ile Thr Ser Ala Arg Leu Leu Gln Gln Glu
                     85                  90                  95

GTT CTG CAG AAC GTC TCG GAT GCT GAG AGC TGT TAC CTT GTC CAC ACC        336
Val Leu Gln Asn Val Ser Asp Ala Glu Ser Cys Tyr Leu Val His Thr
            100                 105                 110

CTG CTG GAG TTC TAC TTG AAA ACT GTT TTC AAA AAC TAC CAC AAT AGA        384
Leu Leu Glu Phe Tyr Leu Lys Thr Val Phe Lys Asn Tyr His Asn Arg
            115                 120                 125

ACA GTT GAA GTC AGG ACT CTG AAG TCA TTC TCT ACT CTG GCC AAC AAC        432
Thr Val Glu Val Arg Thr Leu Lys Ser Phe Ser Thr Leu Ala Asn Asn
130                 135                 140

TTT GTT CTC ATC GTG TCA CAA CTG CAA CCC AGT CAA GAA AAT GAG ATG        480
Phe Val Leu Ile Val Ser Gln Leu Gln Pro Ser Gln Glu Asn Glu Met
145                 150                 155                 160

TTT TCC ATC AGA GAC AGT GCA CAC AGG CGG TTT CTG CTA TTC CGG AGA        528
Phe Ser Ile Arg Asp Ser Ala His Arg Arg Phe Leu Leu Phe Arg Arg
                    165                 170                 175

GCA TTC AAA CAG TTG GAC GTA GAA GCA GCT CTG ACC AAA GCC CTT GGG        576
Ala Phe Lys Gln Leu Asp Val Glu Ala Ala Leu Thr Lys Ala Leu Gly
                180                 185                 190

GAA GTG GAC ATT CTT CTG ACC TGG ATG CAG AAA TTC TAC AAG CTC TGA        624
Glu Val Asp Ile Leu Leu Thr Trp Met Gln Lys Phe Tyr Lys Leu
            195                 200                 205

(2) INFORMATION FOR SEQ ID NO:6:

(i) SEQUENCE CHARACTERISTICS:
        (A) LENGTH: 207 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:6:

Met Asn Phe Gln Gln Arg Leu Gln Ser Leu Trp Thr Leu Ala Ser Arg
 1               5                  10                  15

Pro Phe Cys Pro Pro Leu Leu Ala Thr Ala Ser Gln Met Gln Met Val
                20                  25                  30

Val Leu Pro Cys Leu Gly Phe Thr Leu Leu Leu Trp Ser Gln Val Ser
            35                  40                  45

Gly Ala Gln Gly Gln Glu Phe His Phe Gly Pro Cys Gln Val Lys Gly
        50                  55                  60

Val Val Pro Gln Lys Leu Trp Glu Ala Phe Trp Ala Val Lys Asp Thr
 65                  70                  75                  80

Met Gln Ala Gln Asp Asn Ile Thr Ser Ala Arg Leu Leu Gln Gln Glu
                 85                  90                  95

Val Leu Gln Asn Val Ser Asp Ala Glu Ser Cys Tyr Leu Val His Thr
            100                 105                 110

Leu Leu Glu Phe Tyr Leu Lys Thr Val Phe Lys Asn Tyr His Asn Arg
        115                 120                 125

Thr Val Glu Val Arg Thr Leu Lys Ser Phe Ser Thr Leu Ala Asn Asn
130                 135                 140
```

```
Phe Val Leu Ile Val Ser Gln Leu Gln Pro Ser Gln Glu Asn Glu Met
145                 150                 155                 160

Phe Ser Ile Arg Asp Ser Ala His Arg Arg Phe Leu Leu Phe Arg Arg
            165                 170                 175

Ala Phe Lys Gln Leu Asp Val Glu Ala Ala Leu Thr Lys Ala Leu Gly
        180                 185                 190

Glu Val Asp Ile Leu Leu Thr Trp Met Gln Lys Phe Tyr Lys Leu
        195                 200                 205
```

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

ATTAACCCTC ACTAAAGATC TGACTG                                              26

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

CATTATGCTG AGTGATATCT TTTTTTTTCC                                    30

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GGATGCTCCG ACTGACCC                                                      18

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CTGAGCAACC ATCCACTGCC                                               20

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CGGGATCCGT CGACATGCTG ACTGAGCCTG CCCAAC                                36

(2) INFORMATION FOR SEQ ID NO:12:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GCTCTAGACT CGAGTCACTT GTCATCGTCG TCCTTGTAGT CGAGATGGTA GAATTTCTGC      60

ATCC                                                                  64

(2) INFORMATION FOR SEQ ID NO:13:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

CGGGATCCGT CGACCATTTA GAGACTTGCT CTTGCACT                              38

(2) INFORMATION FOR SEQ ID NO:14:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GCTCTAGACT CGAGTCACTT GTCATCGTCG TCCTTGTAGT CGCTTTTCAT TTTGATCATC      60

ATGTATG                                                               67

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

TTACCCTGCT TCTCTGG                                                    17

-continued (2) INFORMATION FOR SEQ ID NO:16:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:16:

TCCATCAGAG ACAGTCA                17